(12) United States Patent
Stewart et al.

(10) Patent No.: US 6,183,996 B1
(45) Date of Patent: Feb. 6, 2001

(54) NUCLEOTIDE SEQUENCE ENCODING CARBAMOYL PHOSPHATE SYNTHETASE II

(75) Inventors: Thomas S. Stewart, Mirandah; Maria V. Flores; William J. O'Sullivan, both of Randwick, all of (AU)

(73) Assignee: Unisearch Limited, New South Wales (AU)

(*) Notice: Under 35 U.S.C. 154(b), the term of this patent shall be extended for 0 days.

(21) Appl. No.: 09/150,741

(22) Filed: Sep. 10, 1998

Related U.S. Application Data

(63) Continuation-in-part of application No. 08/446,855, filed on Jul. 6, 1995, now Pat. No. 5,849,573.

(30) Foreign Application Priority Data

Dec. 3, 1992 (AU) ................................................. PL-6206
Dec. 16, 1992 (AU) ................................................. PL-6380
Dec. 2, 1993 (AU) ................................................. 00617/93

(51) Int. Cl.$^7$ ........................... C12N 15/09; C12P 19/34; C07H 21/00
(52) U.S. Cl. .................. 435/91.1; 435/91.31; 435/320.1; 536/23.1; 536/24.5
(58) Field of Search .................................. 435/6, 7.22, 32, 435/91.1, 91.31, 320.1, 375; 514/44; 536/23.1, 24.31, 24.32, 24.5

(56) References Cited

U.S. PATENT DOCUMENTS 5,585,479  12/1996  Hoke et al. ........................ 536/24.5

OTHER PUBLICATIONS

Antisense '97: A roundtable on the state of the industry. Nature Biotechnology 15 (Jun. 1997): 519–524.*
Gura, T. Antisense has growing pains. Science 270 (Oct. 1995): 575–577.*
Rojanasakul, Y. Antisense oligonucleotide therapeutics: drug delivery and targeting. Adv. Drug Delivery Rev. 18(1996): 115–131.*
Schofield, J.P., "Molecular studies on an ancient gene . . . ", Clinical Science, vol. 84, No. 2, pp. 119–128 (1993).
Gero, et al., "Pyrimidine De Novo Synthesis During The Life Cycle . . . ", J. Parasit., vol. 70, No. 4, pp. 536–541 (1984).
Lusty, et al., "Yeast Carbamyl Phosphate Synthetase"; Journal of Biological Chemistry, vol. 258, No. 23, pp. 14466–14477 (1983).
Kaseman, et al., "[41] Carbamyl Phosphate Synthesis (Glutamine–Utilizing) . . . ", Methods in Enzymology, vol. 113, pp. 305–326, Academic Press, Inc. (1985).
Aoki, et al., "Regulatory Properties and Behavior of Activity . . . "; The Journal of Biological Chemistry, vol. 257, No. 1, pp. 432–438 (1982).
Hill, et al., "Pyrimidine Biosynthesis in *Plasmodium Berghei*"; Int. J. Biochem., vol. 13, No. 3, pp. 303–310 (1981).
Stull et al, Antigene, ribozyme and aptamer nucleic . . . , Pharm. Res. vol. 12, No. 4 pp. 465–583 (1995).
Chansiri et al, "The structural gene for . . . ," Mol. Biochem. Parasitol, vol. 74, pp. 239–243 (1995).
Gewirtz et al, Facilitating oligonucleotide delivery . . . , Proc. Natl. Acad. Sci. USA vol. 93, pp. 3161–3164 (1996).
Sambrook et al, "Molecular Cloning . . . ," Cold. Spring. Harbour Laboratory Press, pp. 8.51–8.42 (1989).
Lewin, "Genes IV", Oxford University Press, NY, pp. 506–507 (1990).

* cited by examiner

*Primary Examiner*—Robert A. Schwartzman
*Assistant Examiner*—Thomas G. Larson
(74) *Attorney, Agent, or Firm*—Nixon & Vanderhye

(57) ABSTRACT

The present invention provides a nucleotide sequence encoding carbamoyl phosphate synthetase II of *Plasmodium falciparum*. Carbamoyl phosphate synthetase II catalyses the first committed and rate-limiting step in the de novo pyrimidine biosynthetic pathway. *P. falciparum* relies exclusively on pyrimidine synthesis de novo because of its inability to salvage pyrimidines. Mature human red blood cells, however, have no recognized requirement for a pyrimidine nucleotide. Accordingly, this enzyme represents a prime chemotherapeutic locus. The present invention relates to the use of the sequence encoding carbamoyl phosphate synthetase II in the recombinant production of carbamoyl phosphate synthetase II and to antisense molecules, ribozymes and other gene inactivation agents designed from this sequence.

4 Claims, 7 Drawing Sheets

```
         -60  |   -50   |   -40   |   -30   |   -20   |   -10   |
-1225                                         GAATT CCTTCAGCCA AAAAAAATGA -1201
-1200 CAACGCAAAT TTTAAGAAAA GAAAAACAAT CGACTCGTCT TTGAATGAGG TTAGAAATTC -1141
-1140 GATACGTGAA AGGGACTTAA GAAGGCTTAA CAGAGAAAAG AGTAAAATCT TATAAGCATT -1081
-1080 TGAAGGAAAA AATAATAAAA TAAAAAAATA AAAAGATAAA AAATATTTAT ATTTGATATG -1021
-1020 TAGTATATAT AATGATTATT CATATTAATA ACATAGATAA AAAACTTTTT TTTTTTTTTT -961
 -960 TTTTCTTTAT ATTTATTAAC AATACATTTA AGTTATTTTA TATATATATA TATATATATA -901
 -900 TATATATATA TATATATATA TGTTTGTGTG TTCATTTGTT TATAAAATTA CTTGAAATAT -841
 -840 AAAACTTATT AATATATTTC CAATTAATAT GAATACAATT ATTAATATTT TGATGTGTAC -781
 -780 ACATTAATAT AGTTTTACAC TTCTTATAAT AAAACCATCC TATATATTAT ACACAATATA -721
 -720 TAATACTCCC CAATATTGTG GTTCCTATAA TTTTATTTAT ATATTTATTT ATTAATTTAT -661
 -660 TCATTTATTT ATTTTTTTTC TTAGTTTATA AAATAGTAAT TCTACTAATT TAAAAAAAAA -601
 -600 AAAAAAAAAA AAAAAAAAA GAAAAAAAAA AAATTTACAT ATGAAAAATG AACTTGTATA -541
 -540 TGTAAATTTA TAAATATTTT AAACATAAAT ATAAATGTAT AAAAAAAAAA AAGAAAAATG -481
 -480 GGAAAAAATA ATATAGATAT ATATATAAAT ATATATATAT ATATAATTAT TGGGGATATT -421
 -420 CTCTGAATCA TAGGTCTTAA ACAGTTTTAT TCTTTTAACA TCACAAAGTT GTTATTAAAA -361
 -360 GTATATATAT CTTATTGGTT CCTATATAAA ACTATAGTAT TCTATAATAT ATTCTGTATA -301
 -300 TTTCATTTTA TCATTTGTAA GCAATCCCTA TTTATTATAA TTATTATTTT TTTTTTTATA -241
 -240 AAAGAGGTAT AAAACAGTTT ATTCAATTTT TTTCCTAAAG GAGCAACCTT CAGTCAATTT -181
 -180 ACATTTTCCA CCGGTTGGTT GGCACAACAT AATGTTACAG CTAAAAAAAG AAAGAAAAA -121
 -120 AAAAAAAAAA AAAAAAAAAA AAAAATATA TATATATA TATATATATA CATAATATGT -61
  -60 ACAATGCTAC CATACAAGTA TATAAATTTT TCAACATTGT TGTGATGTTG CATTTTTCTT -1
    1 ATGTATATTT CTTTTAAATA TAATTTATAT ATATATATAT ATATATATAT ATATATATTT 60
   61 GTTCTTATAG ATTTTAAAAC AGTTGGGAGG TTAATTCTTG AAGATGGTAA CGAATTTGTA 120
  121 GGGTACAGTG TAGGTTACGA AGGGTGTAAA GGAAATAATA GTATATCATG TCATAAGGAG 180
  181 TATAGAAATA TTATTAATAA TGATAATAGC AAGAATAGTA ATAATTCATT TTGTAATAAT 240
  241 GAAGAAAACA ATTTGAAAGA TGATTTATTA TATAAAAATA GTCGATTAGA AAATGAAGAT 300
  301 TTTATTGTTA CAGGTGAAGT TATATTTAAT ACAGCTATGG TTGGATATCC TGAAGCTTTA 360
  361 ACGGACCCAA GTTATTTTGG TCAAATATTA GTTTTAACAT TTCCTTCTAT TGGTAATTAT 420
  421 GGTATTGAAA AAGTAAAACA TGATGAAACG TTTGGATTAG TACAAAATTT TGAAAGTAAT 480
  481 AAAATTCAAG TACAAGGTTT AGTTATTTGT GAATATTCGA AGCAATCATA TCATTACAAT 540
  541 TCTTATATTA CCTTAAGTGA ATGGTTAAAG ATTTATAAAA TTCCATGTAT AGGTGGTATA 600
  601 GATACAAGAG CCTTAACAAA ACTTTTAAGA GAAAAGGTA GTATGTTAGG TAAAATAGTT 660
  661 ATATATAAAA ACAGACAACA TATTAATAAA TTATATAAAG AAATTAATCT TTTTGATCCT 720
  721 GGTAATATAG ATACTCTAAA ATATGTATGT AATCATTTTA TACGTGTTAT TAAGTTGAAT 780
  781 AATATTACAT ATAATTATAA AAATAAGGAA GAATTTAATT ATACCAATGA AATGATTACT 840
  841 AATGATTCTT CAATGGAAGA TCATGATAAT GAAATTAATG GTAGTATTTC TAATTTTAAT 900
  901 AATTGTCCAA GTATCTCTAG TTTTGATAAA AGTGAATCGA AAAATGTTAT TAATCATACA 960
  961 TTGTTAAGAG ATAAAATGAA CCTAATAACT TCATCTGAAG AATATCTGAA AGATCTTCAT 1020
 1021 AATTGTAATT TTAGTAATAG TAGTGATAAA AATGATTCTT TTTTTAAGTT ATATGGTATA 1080
 1081 TGTGAATATG ATAAATATTT AATTGACCTT GAAGAAAATG CTAGCTTTCA TTATAATAAT 1140
 1141 GTAGATGAAT ATGGATATTA TGATGTTAAT AAAAATACAA ATATTCTATC TAATAATAAA 1200
 1201 ATAGAACAAA ACAACAATAA CGAAAATAAC AAAAATAACA AAATAACAA CAATAACGAG 1260
 1261 GTTGATTATA TAAAGAAAGA TGAGGATAAT AATGTCAATA GTAAGGTCTT TTATAGCCAA 1320
 1321 TATAATAATA ATGCACAAAA TAATGAACAT ACCGAATTTA ATTTAAATAA TGATTATTCT 1380
 1381 ACTTATATTA GAAAGAAAAT GAAAAATGAA GAATTCCTTA ATTTGGTAAA CAAAAGAAAA 1440
 1441 GTAGACCATA AAGAAAAAAT TATTGTTATT GTTGATTGTG GTATTAAAAA TAGTATAATC 1500
 1501 AAAAATTTAA TAAGACACGG TATGGATCTT CCATTAACAT ATATTATTGT ACCTTATTAT 1560
 1561 TACAATTTTA ATCATATAGA TTATGATGCA GTTCTTTTAT CTAATGGTCC TGGAGATCCT 1620
 1621 AAAAAGTGTG ATTTCCTTAT AAAAAATTTG AAAGATAGTT AACAAAAAA TAAAATTATA 1680
 1681 TTTGGTATTT GTTAGGTAA TCAACTATTA GGTATATCAT TAGGTTGTGA CACATATAAA 1740
 1741 ATGGAAATATG GTAATAGAGG TGTTAATCAA CCCGTAATAC AATTAGTAGA TAATATATGT 1800
 1801 TACATTACCT CACAAAATCA TGGATACTGT TTAAAGAAAA AATCAATTTT AAAAGAAAA 1860
 1861 GAGCTTGCGA TTAGTTATAT AAATGCTAAT GATAAATCTA TAGAAGGTAT TTCACATAAA 1920
 1921 AATGGAAGAT TTTATAGTGT CCAGTTTCAT CCTGAGGGTA ATAATGGTCC TGAAGATACA 1980
 1981 TCATTTTTAT TTAAGAATTT TCTTTTAGAT ATCTTTAATA AGAAAAAACA ATATAGAGAA 2040
```

Fig. 2A

```
2041 TATTTAGGAT ATAATATTAT TTATATAAAA AAGAAAGTGC TTCTTTTAGG TAGTGGTGGT 2100
2101 TTATGTATAG GACAAGCAGG AGAATTCGAT TATTCAGGAA CACAAGCAAT TAAAAGTTTA 2160
2161 AAAGAATGTG GTATATATGT TATATTAGTT AATCCTAACA TAGCAACTGT TCAAACATCA 2220
2221 AAAGGTTTGG CAGATAAGGT ATACTTTTTA CCAGTTAATT GTGAATTTGT AGAAAAAATT 2280
2281 ATTAAAAAGG AAAAACCTGA TTTTATTTTA TGTACATTTG GTGGTCAGAC AGCTTTAAAT 2340
2341 TGTGCTTTAA TGTTAGATCA AAAAAAAGTA TTGAAAAAGA ATAATTGTCA ATGTTTAGGT 2400
2401 ACATCTTTAG AATCTATAAG AATAACAGAA AATAGAACAT TATTTGCTGA AAAATTAAAA 2460
2461 GAAATTAATG AAAGAATAGC TCCATATGGT AGTGCAAAAA ATGTTAATCA AGCTATTGAT 2520
2521 ATAGCTAATA AAATAGGATA TCCAATATTA GTACGTACAA CATTTTCGTT AGGAGGATTA 2580
2581 AATAGTAGTT TCATAAATAA TGAAGAAGAA CTTATCGAAA AATGTAATAA AATATTTTA 2640
2641 CAAACTGATA ATGAAATATT TATAGATAAA TCATTACAAG GATGGAAAGA AATAGAATAT 2700
2701 GAATTATTAA GAGATAATAA AAATAATTGT ATAGCTATAT GTAATATGGA AAATATAGAT 2760
2761 CCATTAGGTA TACATACAGG AGATAGTATA GTTGTTGCAC CTTCACAAAC ATTAAGTAAT 2820
2821 TATGAATATT ATAAATTTAG AGAAATAGCA TTAAAGGTAA TTCACATTT AAATATTATA 2880
2881 GGAGAATGTA ATATACAATT TGGTATAAAT CCACAAACAG GAGAATATTG TATTATTGAA 2940
2941 GTTAATGCTA GGCTTAGTAG AAGTTCAGCA TTAGCTTCTA AAGCTACTGG TTATCCACTT 3000
3001 GCTTATATAT CAGCAAAAAT AGCCTTGGGA TATGATTTGA TAAGTTTAAA AAATAGCATA 3060
3061 ACTAAAAAAA CAACTGCCTG TTTTGAACCC TCTCTAGATT ACATTACAAC AAAAATACCA 3120
3121 CGATGGGATT TAAATAAATT TGAGTTTGCT TCTAATACAA TGAATAGTAG TATGAAAAGT 3180
3181 GTAGGAGAAG TTATGTCTAT AGGTAGAACC TTTGAAGAAT CTATACAAAA ATCTTTAAGA 3240
3241 TGTATTGATG ATAATTATTT AGGATTTAGT AATACGTATT GTATAGATTG GGATGAAAAG 3300
3301 AAAATTATTG AAGAATTAAA AAATCCATCA CCAAAAAGAA TTGATGCTAT ACATCAAGCT 3360
3361 TTCCATTTAA ATATGCCTAT GGATAAAATA CATGAGCTGA CACATATTGA TTATTGGTTC 3420
3421 TTACATAAAT TTTATAATAT ATAATAATTTA CAAAATAAGT TGAAAACGTT AAAATTAGAG 3480
3481 CAATTATCTT TTAATGATTT GAAGTATTTT AAGAAGCATG GTTTAGTGA TAAGCAAATA 3540
3541 GCTCACTACT TATCCTTCAA CACAAGCGAT AATAATAATA ATAATAATAA TATTAGCTCA 3600
3601 TGTAGGGTTA CAGAAAATGA TGTTATGAAA TATAGAGAAA AGCTAGGATT ATTTCCACAT 3660
3661 ATTAAAGTTA TTGATACCTT ATCAGCCGAA TTTTCCGGCTT TAACTAATTA TTTATATTTA 3720
3721 ACTTATCAAG GTCAAGAACA TGATGTTCTC CCATTAAATA TGAAAAGGAA AAGATATGC 3780
3781 ACGCTTAATA ATAAACGAAA TGCAAATAAG AAAAAAGTCC ATGTCAAGAA CCACTTATAT 3840
3841 AATGAAGTAG TTGATGATAA GGATACACAA TTACACAAAG AAAATAATAA TAATAATAAT 3900
3901 ATGAATTCTG GAAATGTAGA AAATAAATGT AAATTGAATA AAGAATCCTA TGGCTATAAT 3960
3961 AATTCTTCTA ATTGTATCAA TACAAATAAT ATTAATATAG AAAATAATAT TTGTCATGAT 4020
4021 ATATCTATAA ACAAAAATAT AAAAGTTACA ATAAACAATT CCAATAATTC TATATCGAAT 4080
4081 AATGAAAATG TTGAAACAAA CTTAAATTGT GTATCTGAAA GGGCCGGTAG CCATCATATA 4140
4141 TATGGTAAAG AAGAAAAGAG TATAGGATCT GATGATACAA ATATTTTAAG TGCACAAAAT 4200
4201 TCAAATAATA ACTTTTCATG TAATAATGAG AATATGAATA AAGCAAACGT TGATGTTAAT 4260
4261 GTACTAGAAA ATGATACGAA AAAACGAGAA GATATAAATA CTACAACAGT ATTTATGGAA 4320
4321 GGTCAAAATA GTGTTATTAA TAATAAGAAT AAAGAGAATA GTTCTTTATT GAAAGGTGAT 4380
4381 GAAGAAGATA TTGTGATGGT AAATTTAAAA AAGGAAAATA ATTATAATAG TGTAATTAAT 4440
4441 AATGTAGATT GTAGGAAAAA GGATATGGAT GGAAAAAATA TAAATGATGA ATGTAAAACA 4500
4501 TATAAGAAAA ATAAATATAA AGATATGGGA TTAAATAATA ATATAGTAGA TGAGTTATCC 4560
4561 AATGGAACAT CACATTCAAC TAATGATCAT TTATATTTAG ATAATTTTAA TACATCAGAT 4620
4621 GAAGAAATAG GAATAATAA AAATATGGAT ATGTATTTAT CTAAGGAAAA AAGTATATCT 4680
4681 AATAAAAACC CTGGTAATTC TTATTATGTT GTAGATTCCG TATATAATAA TGAATACAAA 4740
4741 ATTAATAAGA TGAAAGAGTT AATAGATAAC GAAAATTTAA ATGATGAATA TAATAATAAT 4800
4801 GTTAATATGA ATTGTTCTAA TTATAATAAT GCTAGTGCAT TTGTAAATGG AAAGGATAGA 4860
4861 AATGATAATT TAGAAAATGA TTGTATTGAA AAAAATATGG ATCATACATA CAAACATTAT 4920
4921 AATCGTTTAA ACAATCGTAG AAGTACAAAT GAGAGGATGA TGCTTATGGT AAACAATGAA 4980
4981 AAAGAGAGCA ATCATGAGAA GGGCCATAGA AGAAATGGTT TAAATAAAAA AAATAAAGAA 5040
5041 AAAAATATGG AAAAAAATAA GGGAAAAAAT AAAGACAAAA AGAATTATCA TTATGTTAAT 5100
5101 CATAAAGGA ATAATGAATA TAATAGTAAC AATATTGAAT CGAAGTTTAA TAATTATGTT 5160
5161 GATGATATAA ATAAAAAGA ATATTATGAA GATGAAAATG ATATATATTA TTTTACACAT 5220
5221 TCGTCACAAG GTAACAATGA CGATTTAAGT AATGATAATT ATTTAAGTAG TGAAGAATTG 5280
5281 AAATACTGATG AGTATGATGA TGATTATTAT TATGATGAAG ATGAAGAAGA TGACTATGAC 5340
5341 GATGATAATG ATGATGATGA TGATGATGAT GATGATGGGG AGGATGAGGA GGATAATGAT 5400
```

Fig. 2B

```
5401 TATTATAATG ATGATGGTTA TGATAGCTAT AATTCTTTAT CATCTTCAAG AATATCAGAT 5460
5461 GTATCATCTG TTATATATTC AGGGAACGAA AATATATTTA ATGAAAAATA TAATGATATA 5520
5521 GGTTTTAAAA TAATCGATAA TAGGAATGAA AAAGAGAAAG AGAAAAAGAA ATGTTTTATT 5580
5581 GTATTAGGTT GTGGTTGTTA TCGTATTGGT AGTTCTGTAG AATTTGATTG GAGTGCTATA 5640
5641 CATTGTGTAA AGACCATAAG AAAATTAAAC CATAAAGCTA TATTAATAAA TTGTAACCCA 5700
5701 GAAACTGTAA GTACAGATTA TGATGAAAGT GATCGTCTAT ATTTTGATGA AATAACAACA 5760
5761 GAAGTTATAA AATTTATATA TAACTTTGAA AATAGTAATG GTGTGATTAT AGCTTTTGGT 5820
5821 GGACAAACAT CAAATAATTT AGTATTTAGT TTATATAAAA ATAATGTAAA TATATTAGGA 5880
5881 TCAGTGCACA AAGTGTTGAT TGTTGTGAAA ATAGGAATAA ATTTTCGCAC TTATGTGATT 5940
5941 CTTAAAATTG ATCAACCGAA ATGGAATAAA TTTACAAAAT TATCCAAGGC TATACAATTT 6000
6001 GCTAATGAGG TAAAATTTCC TGTATTAGTA AGACCATCGT ATGTATTATC TGGTGCAGCT 6060
6061 ATGAGAGTTG TAAATTGTTT TGAAGAATTA AAAAACTTTT TAATGAAGGC AGCTATTGTT 6120
6121 AGTAAAGATA ATCCTGTTGT AATATCAAAA TTTATTGAGA ATGCTAAAGA AATAGAAATA 6180
6181 GATTGTGTTA GTAAAAATGG TAAAATAATT AATTATGCTA TATCTGAACA TGTTGAAAAT 6240
6241 GCTGGTGTAC ATTCAGGTGA TGCAACATTA ATATTACCTG CACAAAATAT ATATGTTGAA 6300
6301 ACACATAGGA AAATAAAGAA AATATCCGAA AAGATTTCAA AATCATTAAA TATATCTGGT 6360
6361 CCATTTAATA TACAATTTAT ATGTCATCAA AATGAAATAA AAATTATTGA ATGTAATTTA 6420
6421 AGAGCATCTA GAACTTTTCC ATTTATATCA AAAGCTCTAA ATCTAAACTT TATAGATTTA 6480
6481 GCTACAAGGA TATTAATGGG TTATGACGTC AAACCAATTA ATATATCATT AATTGATTTA 6540
6541 GAATATACAG CTGTAAAAGC ACCGATTTTC TCATTTAATA GATTACATGG ATCAGATTGT 6600
6601 ATACTAGGTG TAGAAATGAA ATCTACAGGT GAAGTAGCAT GTTTTGGTTT AAATAAATAT 6660
6661 GAAGCTTTAT TAAAATCATT AATAGCTACA GGTATGAAGT TACCCAAAAA ATCAATACTT 6720
6721 ATAAGTATTA AAAATTTAAA TAATAAATTA GCTTTTGAAG AACCGTTCCA ATTATTATTT 6780
6781 TTAATGGGAT TTACAATATA TGCGACTGAA GGTACGTATG ATTTCTACTC TAAATTTTTA 6840
6841 GAATCTTTTA ATGTTAATAA AGGTTCTAAA TTTCATCAAA GACTTATTAA AGTTCATAAT 6900
6901 AAAAATGCAG AAAATATATC ACCAAATACA ACAGATTTAA TTATGAATCA TAAAGTTGAA 6960
6961 ATGGTTATTA ATATAACTGA TACATTAAAA ACAAAGGTTA GTTCAAATGG TTATAAAATT 7020
7021 AGAAGATTAG CATCAGATTT CCAGGTTCCT TTAATAACTA ATATGAAACT TTGTTCTCTT 7080
7081 TTTATTGACT CATTATATAG AAAATTCTCA AGACAAAAGG AAAGAAAATC ATTCTATACC 7140
7141 ATAAAGAGTT ATGACGAATA TATAAGTTTG GTATAAGCAA GAAATTATTC AATAAATTCG 7200
7201 ATTTAACATT ACTTATTTAT GTATTTATTA ACTTTCATTC CATAACAACA TGAAAAGTAT 7260
7261 AAATATATAA ATAGTAATAT ATAATATATA ATATATATAT ATATATATAT ATATATATTT 7320
7321 ATTTATTTAA TTATATTTAC GTTTAAATAT TAATAAATGT TTTTATTAAA TATGATCATT 7380
7381 AATTTATATT GATTTATTTT TTTATAAATT TTGTTATAT ATACAAATTT TATTTATTCA 7440
7441 CTCATATGTA TAAACCAAAA TGGTTTTTTC AATTTACAAA TAATTTTATA ATTTTAATAA 7500
7501 ATTTATTAAT TATAAAAAAA ATAAAAATAT ATAAACATTA AAATGTATAA ATTCTTTTAA 7560
7561 TTATATAATA ATTTATAAAT GTTATGATTT TTTTAAAAAA TTCAACGAAA AAAAAGAGGA 7620
7621 ACTGTATATA CAAAAGGGAC TATATATATG TATATATATA TATATATATA TATGTTTTTT 7680
7681 TTTCCTTATT CTAGA                                                7695
         |   10     |   20     |   30     |   40     |   50     |   60
```

Fig. 2C

```
                              790        800         810        820        830         840
                              --AU        A        AAGGA      UU   AUUA      A     AAUG     CUA      U
                         UAC     AUAAUUAU AAAAU    AGAA   UA    UACCA  UGA    AUUA    AUGAU
CPSRz1
M10                      AUG    UG UUAAUA UUUUA    UCUU   AU    AUGGU  AUU    UAAU    UACUA
                         AACC       A     ----A    -U    ---G    A    AAAG    -AG        -
                              910        900         890        880        870         860
                                   920        930
```

```
                         3700      3710        3720           -         3730       3740
                          U         A   AU      -    AA    A    ------A   UCA        AU
CPSRz4                  UUAACUA  UU   UUAUA   UUU   CUU  UCA           G      AGAAC
M15                     AGUUGAU  AA   AAUAU   AAA   GAA  AGU           CC     UCUUG   G
                         -        G   GU       A    -G    A    AUAAAUUA   -C       UA
                         3850      3840        3770        3760          3750
```

M17

```
     5220
A    -
CA  CAUU   C GUC A  CA
GU  GUAG    GUAGU   GU
-    A              A
           5300
```

M18

```
                      5700      5710       5720
                    -A    C    A      G -  -G             AA
              UUGU   ACC  AGAA  CUGUAA  UACA  AUUAU  GAUGA   G
              AACA   UGG  UUUU  AAUAU   GUGU  UAAUG  CUG CU  U
                GG    -    C     A       GG          AG
                5820       5810         5800       5730
                                              5740       5750
                                              UA    - -   A   AA
                                              UAUUU    UG    UG
                                              AUAAA    AC    AC
                                              - -      AG    A  AA
                                              5790   5760
```

Fig. 3

| ANTISENSE | SEQUENCE | TARGET |
|---|---|---|
| M9 | TTT TCT AAT CGA CTA TTT TTA | pfCPSII |
| M10 | GAG ATA CTT GGA CAA TTA TTA | pfCPSII |
| M11 | CCT TAC TAT TGA CAT TAT TAT | pfCPSII |
| M12 | GGC TAT AAA AGA CCT TAC TAT | pfCPSII |
| M13 | GGA TCT CCA GGA CCA TTA GAT | pfCPSII |
| M14 | CCT AAA CAT TGA CAA TTA TTC | pfCPSII |
| M15 | TCA TGT TCT TGA CCT TGA TAA | pfCPSII |
| M16 | GAT ATA TCA TGA CAA ATA TTA | pfCPSII |
| M17 | GTT ACC TTG TGA CGA ATG TGT | pfCPSII |
| M18 | TCA TTT TGA TGA CAT ATA AAT | pfCPSII |
| M21 | AAC ATC ATG TTC TTG ACC TTG ATA AGT TA | pfCPSII |
| M19 | CGT CGG AAC TGA ATT TGG CTC | – |
| M20 | CCT CAG TGC TGA CAG CCC ATC | – |

Fig. 4A

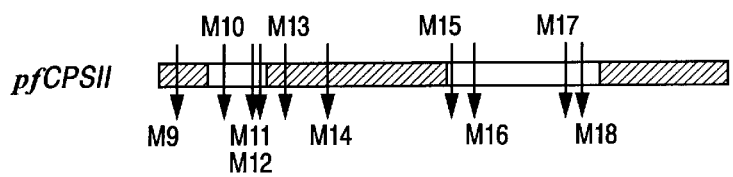

Fig. 4B

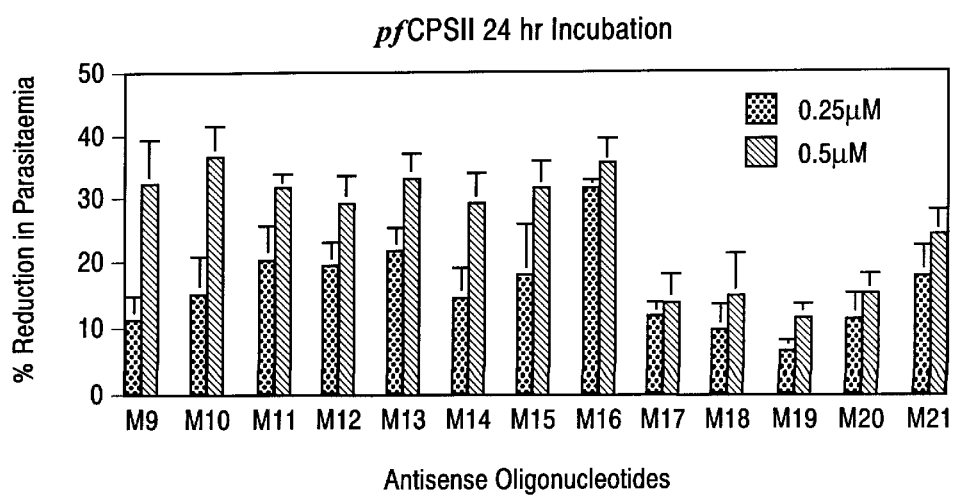

Fig. 4C

NUCLEOTIDE SEQUENCE ENCODING CARBAMOYL PHOSPHATE SYNTHETASE II

This application is a continuation-in-part of application Ser. No. 08/446,885, filed Jul. 6, 1995, now U.S. Pat. No. 5,849,573.

FIELD OF THE INVENTION

The present invention relates to nucleotide sequences encoding carbamoyl phosphate synthetase II of *Plasmodium falciparum*, to methods of producing this enzyme using recombinant DNA technology and to the use of this sequence and enzyme in the design of therapeutics.

BACKGROUND OF THE INVENTION

The urgency for the design of novel chemotherapeutic agents for the treatment of malaria has been renewed in recent times due to the evolution of human malarial parasites, primarily *Plasmodium falciparum*, which are resistant to traditional drugs. Research into a vaccine seems a very plausible alternative, but after years of investigation, no clinically acceptable product has come to date. At the same time, there is also an increasing decline in the efficacy of insecticides against mosquito vectors. At present, more than two-thirds of the world's population—approximately 500 million people—are thought to live in malaria areas (Miller, 1989). It ranks eighth in the World Health Organization's (WHO) list of ten most prevalent diseases of the world (270 million infections a year) and ranks ninth of the ten most deadly diseases, claiming over 2 million lives a year (Cox, 1991; Marshall, 1991). Though chiefly confined to poor nations, there are recent reports of infections in the United States (Marshall, 1991) and Australia (Johnson, 1991), and ever increasing cases of travellers' malaria (Steffen and Behrens, 1992).

Comparative biochemical studies between the malaria parasite, *P. falciparum* and its host have revealed differences in a number of metabolic pathways. One such distinction is that the parasite relies exclusively on pyrimidine synthesis de novo because of its inability to salvage preformed pyrimidines (Sherman, 1979). Moreover, the mature human red blood cell has no recognised requirement for pyrimidine nucleotides (Gero and O'Sullivan, 1990). Major efforts have been directed towards the development of inhibitors of the pyrimidine biosynthetic pathway (Hammond et al., 1985; Scott et al., 1986; Prapunwattana et al., 1988; Queen et al., 1990; Krungkrai et al., 1992), confirming its potential as a chemotherapeutic locus. Current research into the molecular biology of the key pyrimidine enzymes is envisioned as a powerful tool, not only to get a better understanding of the parasite's biochemistry, but also to explore specific differences between the parasite and the mammalian enzymes.

Glutamine-dependent carbamoyl phosphate synthetase (CPSU, EC 6.3.5.5) catalyses the first committed and rate-limiting step in the de novo pyrimidine biosynthetic pathway of eukaryotic organisms (Jones, 1980). Moreover, because it catalyzes a complex reaction involving three catalytic units and several substrates and intermediates, it is a very interesting enzyme to study from a biochemical point of view. The structural relationship of CPSII to other pyrimidine enzymes varies in different organisms, making it a good subject for evolutionary studies.

The paucity of material that can be obtained from malarial cultures has hampered the isolation of adequate amounts of pure protein for analysis. The difficulty in purifying CPS is further augmented by its inherent instability. Studies using crude extracts from *P. berghei* (a rodent malaria) revealed a high molecular weight protein containing CPS activity, which was assumed to be associated with ATCase (Hill et al., 1981), a situation also found in yeast (Makoff and Radford, 1978). However, recent analysis by Krungkrai and co-workers (1990) detected separate CPSII and ATCase activities in *P. berghei*. Although CPS activity has been detected in *P. falciparum* (Reyes et al., 1982) until this current study there is no indication of its size nor its linkage with other enzymes in the pathway.

The glutamine-dependent activity of CPSII can be divided into two steps: (1) a glutaminase (GLNase) reaction which hydrolyzes glutamine (Gln) and transfers ammonia to the site of the carbamoyl phosphate synthetase; and (2) a synthetase reaction, where carbamoyl phosphate is synthesised from two molecules of adenosine triphosphate (ATP), bicarbonate and ammonia. The second activity involves three partial reactions: (a) the activation of bicarbonate by ATP; (b) the reaction of the activated species carboxyphosphate with ammonia to form carbamate; and (c) the ATP-dependent phosphorylation of carbamate to form carbamoyl phosphate (powers and Meister, 1978). Hence, there are two major domains in CPSII, the glutamine amidotransferase domain (GAT) and the carbamoyl phosphate synthetase domain (CPS) or simply synthetase domain. The glutaminase domain (GLNase) is a subdomain of GAT, while there are two ATP-binding subdomains in the synthetase domain.

In view of the similarities between the glutamine amidotransferase domain of CPS and other amidotransferases, it has been proposed that these subunits arose by divergent evolution from a common ancestral gene (=20 kDa) representing the GLNase domain and that particular evolution of the CPS GAT domain (=42 kDa which includes the putative structural domain only present in CPS) must have involved fusions and/or insertions of other sequences (Werner et al., 1935). The GAT of mammalian CPSI gene has been proposed to be formed by a simple gene fusion event at the 5' end of this ancestral gene with an unknown gene (Nyunoya et al., 1985).

The genes for the larger synthetase domains of various organisms were postulated to have undergone a gene duplication of an ancestral kinase gene resulting in a polypeptide with two homologous halves (Simmer et al., 1990). Unlike the subunit structure of *E. coli* and arginine-specific CPS of yeast, a further fusion of the genes encoding GAT and the synthetase domains was suggested to have formed the single gene specific for pyrimidine biosynthesis in higher eukaryotes. Conversely, Simmer and colleagues (1990) proposed that the arginine-specific CPS's (like cpa1 and cpa2 in yeast) as well as rat mitochondrial CPSI arose by defusion from the pyrimidine chimera.

DESCRIPTION OF THE INVENTION

The present inventors have isolated and characterised the complete gene encoding the CPSII enzyme from *P. falciparum* (pfCPSII). Reported here is the sequence including 5' and 3' untranslated regions. In so doing, the present inventors have identified the respective glutaminase and synthetase domains. Unlike CPSII genes in yeast, *D. discoideum*, and mammals, there is no evidence for linkage to the subsequent enzyme, aspartate transcarbamoylase (ATCase). This is in contrast to the report by Hill et al., (1981) for the enzymes from *P. berghei*. The present inventors have, however, found two large inserts in the *P. falciparum* gene of a nature that does not appear to have been previously described.

Accordingly, in a first aspect, the present invention consists in a nucleic acid molecule encoding carbamoyl phosphate synthetase II of *Plasmodium falciparum*, the nucleic acid molecule including a sequence substantially as shown in Table 1 from 1 to 7176, or from 1 to 750, or from 751 to 1446, or from 1447 to 2070, or from 2071 to 3762, or from 3763 to 5571, or from 5572 to 7173, of from 1 to 3360, or from 2071 to 6666, or from 2071 to 7173, or a functionally equivalent sequence.

In a preferred embodiment of the present invention, the nucleic acid molecule includes a sequence shown in Table 1 from −1225 to 7695 or a functionally equivalent sequence.

In a second aspect, the present invention consists in an isolated polypeptide, the polypeptide including an amino acid sequence substantially as shown in Table 1 from 1 to 2391, from 483 to 690, from 691 to 1254, 1858 to 2391, from 1 to 1120, from 691 to 2222, or from 691 to 2391.

As used herein the term "functionally equivalent sequence" is intended to cover minor variations in the nucleic acid sequence which, due to degeneracy in the code, do not result in the sequence encoding a different polypeptide.

In a third aspect the present invention consists in a method of producing *Plasmodium falciparum* carbamoyl phosphate synthetase II, the method comprising culturing a cell transformed with the nucleic acid molecule of the first aspect of the present invention under conditions which allow expression of the nucleic acid sequence, and recovering the expressed carbamoyl phosphate synthetase II.

The cells may be either bacteria or eukaryotic cells. Examples of preferred cells include *E.coli*, yeast, and *Dictyostelium discoideum*.

As will be readily understood by persons skilled in this field, the elucidation of the nucleotide sequence for CPSII enables the production of a range of therapeutic agents. These include antisense nucleotides, ribozymes, and the targeting of RNA and DNA sequences using other approaches, e.g., triplex formation.

As can be seen from a consideration of the sequence set out in Table 1 the *Plasmodium falciparum* CPSII gene includes two inserted sequences not found in other carbamoyl phosphate synthetase genes. The first inserted sequence separates the putative structural domain and the glutiminase domain whilst the second inserted sequence separates the two ATP binding subdomains of the synthetase subunit CPSa and CPSb.

TABLE 1

Nucleotide and Deduced
Amino Acid Sequence of the Carbamoyl Phosphate
Synthetase II Gene from *Plasmodium falciparum* [SEQ ID NOS:1 and 2]

```
-1225 GAATTCCTTCAGCCAAAAAAAATGACAACGCAAATTTTAAGAAAAGAAAAACAATCGACT -1156

-1165 CGTCTTTGAATGAGGTTAGAAATTCGATACGTGAAAGGGACTTAAGAAGGCTTAACAGAG -1106

-1105 AAAAGAGTAAAATCTTATAAGCATTTGAAGGAAAAAATAATAAAATAAAAAAATAAAAAG -1046

-1045 ATAAAAAATATTTATATTTGATATGTAGTATATATAATGATTATTCATATTAATAACATA -986

-985 GATAAAAAACTTTTTTTTTTTTTTTTTTCTTTATATTTATTAACAATACATTTAAGTTA  -926

-925 TTTTATATATATATATATATATATATATATATATATATATATATGTTTGTGTGTTCAT  -866

-865 TTGTTTATAAAATTACTTGAAATATAAAACTTATTAATATATTTCCAATTAATATGAATA  -806

-805 CAATTATTAATATTTTCATGTGTACACATTAATATAGTTTTACACTTCTTATAATAAAAC  -746

-745 CATCCTATATATTATACACAATATATAATACTCCCCAATATTGTGGTTCCTATAATTTTA  -686

-685 TTTATATATTTATTTATTAATTTATTCATTTATTTATTTTTTTTCTTAGTTTATAAAATA  -626

-625 GTAATTCTACTAATTTAAAAAAAAAAAAAAAAAAAAAAAAAAAAAGAAAAAAAAAAAATT  -566

-565 TACATATGAAAAATGAACTTGTATATGTAAATTTATAAATATTTTAAACATAAATATAAA  -506

-505 TGTATAAAAAAAAAAAAGAAAAATGGGAAAAAATAATATAGATATATATATAAATATATA  -446

-445 TATATATATAATTATTGGGGATATTCTCTGAATCATAGGTCTTAAACAGTTTTATTCTTT  -385
```

TABLE 1-continued

Nucleotide and Deduced
Amino Acid Sequence of the Carbamoyl Phosphate
Synthetase II Gene from *Plasmodium falciparum* [SEQ ID NOS:1 and 2]

```
-385 TAACATCACAAAGTTGTTATTAAAAGTATATATATCTTATTGGTTCCTATATAAAACTAT -326

-325 AGTATTCTATAATATATTCTGTATATTTCATTTTATCATTTGTAAGCAATCCCTATTTAT -266

-265 TATAATTATTATTTTTTTTTTTATAAAAGAGGTATAAAACAGTTTATTCAATTTTTTTCC -206

-205 TAAAGGAGCAACCTTCAGTCAATTTACATTTTCCACCGGTTGGTTGGCACAACATAATGT -146

-145 TACAGCTAAAAAAAGAAAGAAAAAAAAAAAAAAAAAAAAAAAAAAAAAAAATATATATAT -86

-85 ATATATATATATATACATAATATGTACAATGCTACCATACAAGTATATAAATTTTTCAAC -26

-25 ATTGTTGTGATGTTGCATTTTTCTT                                      -1

1 ATGTATATTTCTTTTAAATATAATTTATATATATATATATATATATATATATATATATTT 60
   1 M  Y  I  S  F  K  Y  N  L  Y  I  Y  I  Y  I  Y  I  Y  I  F   20

61 GTTCTTATAGATTTTAAAACAGTTGGGAGGTTAATTCTTGAAGATGGTAACGAATTTGTA 120
  21 V  L  I  D  F  K  T  V  G  R  L  I  L  E  D  G  N  E  F  V   40

121 GGGTACAGTGTAGGTTACGAAGGGTCTAAAGGAAATAATAGTATATCATGTCATAAGGAG 180
  41 G  Y  S  V  G  Y  E  G  C  K  G  N  N  S  I  S  C  H  K  E   60

181 TATAGAAATATTATTAATAATGATAATAGCAAGAATAGTAATAATTCATTTTGTAATAAT 240
  61 Y  R  N  I  I  N  N  D  N  S  K  N  S  N  N  S  F  C  N  N   80

241 GAACAAAACAATTTGAAAGATCATTTATTATATAAAAATAGTCGATTAGAAAATGAAGAT 300
  81 E  E  N  N  L  K  D  D  L  L  Y  K  N  S  R  L  E  N  E  D  100

301 TTTATTGTTACAGGTGAAGTTATATTTAATACAGCTATGGTTGGATATCCTGAAGCTTTA 360
 101 F  X  V  T  G  E  V  Z  F  N  T  A  M  V  G  Y  P  E  A  L  120

361 ACGGACCCAAGTTATTTTGGTCAAATATTAGTTTTAACATTTCCTTCTATTGGTAATTAT 420
 121 T  D  P  S  Y  F  G  Q  I  L  V  L  T  F  P  S  I  G  N  Y  140

421 GGTATTGAAAAAGTAAAACATGATGAAACGTTTGGATTAGTACAAAATTTTGAAAGTAAT 480
 141 G  I  E  K  V  K  H  D  E  T  F  G  L  V  Q  N  F  E  S  N  160

481 AAAATTCAAGTACAAGGTTTAGTTATTTGTGAATATTCGAAGCAATCATATCATTACAAT 540
 161 K  X  Q  V  Q  G  L  V  X  C  E  Y  S  K  Q  S  Y  H  Y  N  180

541 TCTTATATTACCTTAAGTGAATGGTTAAAGATTTATAAAATTCCATGTATAGGTGCTATA 600
 181 S  Y  I  T  L  S  E  W  L  K  I  Y  K  I  P  C  I  G  G  I  200

601 GATACAAGAGCCTTAACAAAACTTTTAAGAGAAAAAGGTAGTATGTTAGGTAAAATACTT 660
 201 D  T  R  A  L  T  K  L  L  R  E  K  G  S  M  L  G  K  I  V  220

661 ATATATAAAAACAGACAACATATTAATAAATTATATAAAGAAATTAATCTTTTTGATCCT 720
 221 I  Y  K  N  R  Q  H  I  N  K  L  Y  K  E  I  N  L  F  D  P  240

721 GGTAATATAGATACTCTAAAATATGTATGTAATCATTTTATACGTGTTATTAAGTTGAAT 780
 241 G  N  I  D  T  L  K  Y  V  C  N  H  F  I  R  V  I  K  L  N  260

781 AATATTACATATAATTATAAAAATAAGGAAGAATTTAATTATACCAATGAAATGATTACT 840
 261 N  I  T  Y  N  Y  K  N  K  E  E  F  N  Y  T  N  E  N  I  T  280
```

TABLE 1-continued

Nucleotide and Deduced
Amino Acid Sequence of the Carbamoyl Phosphate
Synthetase II Gene from *Plasmodium falciparum* [SEQ ID NOS:1 and 2]

```
 841 AATGATTCTTCAATGGAAGATCATGATAATGAAATTAATGGTAGTATTTCTAATTTTAAT  900
 281 N  D  S  S  M  E  D  H  D  N  Z  I  N  G  S  I  S  N  F  N   300

901 AATTGTCCAAGTATCTCTAGTTTTGATAAAAGTGAATCGAAAAATGTTATTAATCATACA  960
 301 N  C  P  S  I  S  S  F  D  K  S  E  S  K  N  V  I  N  H  T   320

961 TTGTTAAGAGATAAAATGAACCTAATAACTTCATCTGAAGAATATCTGAAACATCTTCAT 1020
 321 L  L  R  D  K  M  N  L  I  T  S  S  E  E  Y  L  K  D  L  H   340

1021 AATTGTAATTTTAGTAATAGTAGTGATAAAAATGATTCTTTTTTTAAGTTATATGGTATA 1080
 341 N  C  N  F  S  N  S  S  D  K  N  D  S  F  F  K  L  Y  G  I   360

1021 TGTGAATATGATAAATATTTAATTGACCTTGAAGAAAATGCTAGCTTTCATTATAATAAT 1140
 351 C  E  Y  D  K  Y  L  I  D  L  E  E  N  A  S  F  H  Y  N  N   380

1141 GTAGATGAATATGGATATTATGATGTTAATAAAAATACAAATATTCTATCTAATAATAAA 1200
 381 V  D  E  Y  G  Y  Y  D  V  N  K  N  T  N  I  L  S  N  N  K   400

1201 ATAGAACAAAACAACAATAACGAAAATAACAAAAATAACAAAAATAACAACAATAACGAG 1260
 401 I  E  Q  N  N  N  N  Z  N  N  K  N  N  K  N  N  N  N  N  E   420

1261 GTTGATTATATAAAGAAAGATGAGGATAATAATGTCAATAGTAAGGTCTTTTATAGCCAA 1320
 421 V  D  Y  I  K  K  D  E  D  N  N  V  N  S  K  V  F  Y  S  Q   440

1321 TATAATAATAATGCACAAAATAATGAACATACCGAATTTAATTTAAATAATGATTATTCT 1380
 441 Y  N  N  N  A  Q  N  N  E  H  T  E  F  N  L  N  N  D  Y  S   460

1381 ACTTATATTAGAAAGAAAATGAAAAATCAAGAATTCCTTAATTTGGTAAACAAAAGAAAA 1440
 461 T  Y  I  R  K  K  M  K  N  E  E  F  L  N  L  V  N  K  R  K   480

1441 GTAGACCATAAAGAAAAAATTATTGTTATTGTTGATTGTGGTATTAAAAATAGTATAATC 1500
 481 V  D  H  K  E  K  I  I  V  I  V  D  C  G  I  K  N  S  I  I   500

1501 AAAAATTTAATAAGACACGGTATGGATCTTCCATTAACATATATTATTGTACCTTATTAT 1560
 501 K  N  L  I  R  H  G  M  D  L  P  L  T  Y  I  I  V  P  Y  Y   520

1561 TACAATTTTAATCATATAGATTATGATGCAGTTCTTTTATCTAATGGTCCTGGAGATCCT 1620
 521 Y  N  F  N  H  I  D  Y  D  A  V  L  L  S  N  G  P  G  D  P   540

1621 AAAAAGTGTGATTTCCTTATAAAAAATTTGAAAGATAGTTTAACAAAAAATAAAATTATA 1680
 541 K  K  C  D  F  L  I  K  N  L  K  D  S  L  T  K  N  K  I  I   560

1681 TTTGGTATTTGTTTAGGTAATCAACTATTAGGTATATCATTAGGTTGTGACACATATAAA 1740
 561 F  G  I  C  L  G  N  Q  L  L  G  I  S  L  G  C  D  T  Y  K   580

1741 ATGAAATATGGTAATAGAGGTGTTAATCAACCCGTAATACAATTAGTAGATAATATATGT 1800
 581 M  K  Y  G  N  R  G  V  N  Q  P  V  I  Q  L  V  D  N  I  C   600

1801 TACATTACCTCACAAAATCATGGATACTGTTTAAAGAAAAAATCAATTTTAAAAAGAAAA 1860
 601 Y  I  T  S  Q  N  H  G  Y  C  L  K  K  K  S  I  L  K  R  K   620

1861 GAGCTTGCGATTAGTTATATAAATGCTAATGATAAATCTATACAAGGTATTTCACATAAA 1920
 621 E  L  A  I  S  Y  I  N  A  N  D  I  S  I  E  G  I  S  H  K   640

1921 AATGGAAGATTTTATAGTGTCCAGTTTCATCCTCAGGGTAATAATGGTCCTGAAGATACA 1980
```

TABLE 1-continued

Nucleotide and Deduced
Amino Acid Sequence of the Carbamoyl Phosphate
Synthetase II Gene from Plasmodium falciparum [SEQ ID NOS:1 and 2]

```
  641 N  G  R  F  Y  S  V  Q  F  H  F  E  G  N  N  G  P  E  D  T   660

1981 TCATTTTTATTTAACAATTTTCTTTTAGATATCTTTAATAAGAAAAAACAATATAGAGAA 2040
  661 S  F  L  F  K  N  F  L  L  D  I  F  N  K  K  Q  Y  R  E   680

2041 TATTTAGGATATAATATTATTTATATAAAAAAGAAAGTGCTTCTTTTAGGTAGTGGTGGT 2100
  681 Y  L  G  Y  N  I  I  Y  I  K  K  K  V  L  L  G  S  G  G   700

2101 TTATGTATAGGACAAGCAGCACAATTCGATTATTCAGGAACA(AAGCAATTAAAAGTTTA 2160
  701 L  C  I  G  Q  A  G  E  F  D  Y  S  G  T  Q  A  I  K  S  L   720

2161 AAAGAATGTGGTATATATGTTATATTAGTTAATCCTAACATAGCAACTGTTCAAACATCA 2220
  721 K  E  C  G  I  Y  V  I  L  V  N  F  N  I  A  T  V  Q  T  S   740

2221 AAAGGTTTGGCAGATAAGGTATACTTTTTACCAGTTAATTGTGAATTTGTAGAAAAAATT 2280
  741 K  G  L  A  D  K  V  Y  F  L  P  V  N  C  E  F  V  E  K  I   760

2281 ATTAAAAAGGAAAAACCTGATTTTATTTTATGTACATTTGGTGGTCACACAGCTTTAAAT 2340
  761 I  K  K  E  K  P  D  F  I  L  C  T  F  G  G  Q  T  A  L  N   780

2341 TGTGCTTTAATGTTAGATCAAAAAAAAGTATTGAAAAAGAATAATTGTCAATGTTTAGGT 2400
  781 C  A  L  M  L  D  Q  K  K  V  L  K  K  N  N  C  C  C  L  G   800

2401 ACATCTTTAGAATCTATAAGAATAACAGAAAATAGAACATTATTTGCTGAAAAATTAAAA 2460
  801 T  S  L  E  S  I  R  I  T  E  N  R  T  L  F  A  E  K  L  K   820

2461 GAAATTAATGAAAGAATAGCTCCATATGGTAGTGCAAAAAATGTTAATCAAGCTATTGAT 2520
  821 E  I  N  E  R  I  A  P  Y  G  S  A  K  N  V  N  Q  A  I  D   840

2521 ATAGCTAATAAAATAGGATATCCAATATTAGTACGTACAACATTTTCGTTAGGAGGATTA 2580
  841 I  A  N  K  I  G  Y  P  I  L  V  R  T  T  F  S  L  G  G  L   860

2581 AATAGTAGTTTCATAAATAATGAAGAAGAACTTATCGAAAAATGTAATAAAATATTTTTA 2640
  861 N  S  S  F  I  N  N  E  E  E  L  I  E  K  C  N  K  I  F  L   880

2641 CAAACTGATAATGAAATATTTATAGATAAATCATTACAAGGATGGAAAGAAATAGAATAT 2700
  881 Q  T  D  N  E  T  F  I  D  K  S  L  Q  G  W  K  E  I  E  Y   900

2701 GAATTATTAAGAGATAATAAAAATAATTGTATAGCTATATGTAATATGGAAAATATAGAT 2760
  901 E  J  L  R  D  N  K  N  N  C  I  A  I  C  N  M  E  N  I  D   920

2761 CCATTAGGTATACATACAGGAGATAGTATAGTTGTTGCACCTTCACAAACATTAAGTAAT 2820
  921 P  L  G  I  H  T  G  D  S  I  V  V  A  P  S  Q  T  L  S  N   940

2821 TATGAATATTATAAATTTAGAGAAATAGCATTAAAGGTAATTACACATTTAAATATTATA 2880
  941 Y  L  Y  Y  K  F  R  E  I  A  L  K  V  I  T  H  L  N  I  I   960

2881 GGAGAATGTAATATACAATTTGGTATAAATCCACAAACAGGAGAATATTGTATTATTGAA 2940
  961 G  E  C  N  I  Q  F  G  I  N  P  Q  T  G  E  Y  C  I  I  E   980

2941 GTTAATGCTAGGCTTAGTAGAAGTTCAGCATTACCTTCTAAAGCTACTGGTTATCCACTT 3000
  981 V  N  A  R  L  S  R  S  S  A  L  A  S  K  A  T  G  Y  P  L  1000

3001 GCTTATATATCAGCAAAAATAGCCTTGGGATATGATTTGATAAGTTTAAAAAATAGCATA 3060
 1001 A  Y  I  S  A  K  I  A  L  G  Y  D  L  I  S  L  K  N  S  I  1020

3061 ACTAAAAAAACAACTGCCTGTTTTGAACCCTCTCTAGATTACATTACAACAAAAATACCA 3120
```

TABLE 1-continued

Nucleotide and Deduced
Amino Acid Sequence of the Carbamoyl Phosphate
Synthetase II Gene from *Plasmodium falciparum* [SEQ ID NOS:1 and 2]

```
1021 T  K  K  T  T  A  C  F  E  P  S  L  D  Y  I  T  T  K  I  P  1040

3121 CGATCGGATTTAAATAAATTTGAGTTTGCTTCTAATACAATGAATAGTAGTATGAAAAGT 3180
1041 R  W  D  L  N  K  F  E  F  A  S  N  T  M  N  S  S  M  K  S  1060

3181 GTAGGAGAAGTTATGTCTATAGGTAGAACCTTTGAAGAATCTATACAAAAATCTTTAAGA 3240
1061 V  G  E  V  M  S  I  G  R  T  F  E  E  S  I  Q  K  S  L  R  1080

3241 TGTATTGATGATAATTATTTAGGATTTAGTAATACGTATTGTATAGATTGGGATGAAAAG 3300
1081 C  I  D  D  N  Y  L  G  F  S  N  T  Y  C  I  D  W  D  E  K  1100

3301 AAAATTATTCAAGAATTAAAAAATCCATCACCAAAAAGAATTGATGCTATACATCAAGCT 3360
1101 K  I  I  E  E  L  K  N  P  S  P  K  R  I  D  A  I  H  Q  A  1120

3361 TTCCATTTAAATATGCCTATGGATAAAATACATGAGCTGACACATATTGATTATTGGTTC 3420
1121 F  H  L  N  M  P  M  D  K  I  H  E  L  T  H  I  D  Y  W  F  1140

3421 TTACATAAAATTTTATAATATATATAATTTAGAAAATAAGTTGAAAACGTTAAAATTAGAG 3480
1141 L  H  K  F  Y  N  I  Y  N  L  Q  N  K  L  K  T  L  K  L  E  1160

3481 CAATTATCTTTTAATGATTTGAAGTATTTTAAGAAGCATGGTTTTAGTGATAAGCAAATA 3540
1161 Q  L  S  F  N  D  L  X  Y  F  K  K  W  G  F  S  D  K  Q  I  1180

3541 GCTCACTACTTATCCTTCAACACAAGCGATAATAATAATAATAATAATAATATTAGCTCA 3600
1181 A  H  Y  L  S  F  N  T  S  D  N  N  N  N  N  N  N  I  S  S  1200

3601 TGTAGGGTTACAGAAAATGATGTTATGAAATATA&AGAAAAGCTAGGATTATTTCCACAT 3660
1201 C  R  V  T  E  N  D  V  M  K  Y  R  E  K  L  G  L  F  P  H  1220

3661 ATTAAAGTTATTGATACCTTATCAGCCGAATTTCCGGCTTTAACTAATTATTTATATTTA 3720
1221 I  K  V  I  D  T  L  S  A  E  F  P  A  L  T  N  Y  L  Y  L  1240

3721 ACTTATCAAGGTCAAGAACATGATGTTCTCCCATTAAATATGAAAAGGAAAAAGATATGC 3780
1241 T  Y  Q  G  Q  E  H  D  V  L  P  L  N  M  K  R  K  K  I  C  1260

3781 ACGCTTAATAATAAACGAAATGCAAATAAGAAAAAAGTCCATGTCAAGAACCACTTATAT 3840
1261 T  L  N  N  K  R  N  A  N  K  K  K  V  R  V  K  N  X  L  Y  1280

3841 AATGAAGTAGTTGATGATAAGGATACACAATTACACAAAGAAAATAATAATAATAATAAT 3900
1281 N  E  V  V  D  D  K  D  T  Q  L  H  K  E  N  N  N  N  N  N  1300

3901 ATGAATTCTGGAAATGTAGAAAATAAAGTAAATTGAATAAAGAATCCTATGGCTATAAT 3960
1301 M  N  S  G  N  V  E  N  K  C  K  L  N  K  E  S  Y  G  Y  N  1320

3961 AATTCTTCTAATTGTATCAATACAAATAATATTAATATAGAAAATAATATTTGTCATGAT 4020
1321 N  S  S  N  G  I  N  T  N  N  I  N  I  E  N  N  I  C  H  D  1340

4021 ATATCTATAAACAAAAATATAAAAGTTACAATAAACAPLTTCCAATAATTCTATATCAAT 4080
1341 I  S  I  N  K  N  I  K  V  T  I  N  N  S  N  N  S  I  S  N  1360

4081 AATGAAAATGTTGAAACAAACTTAAATTGTGTATCTGAAAGGGCCGGTAGCCATCATATA 4140
1361 N  E  N  V  E  T  N  L  N  C  V  S  E  R  A  G  S  H  H  I  1380

4141 TATGGTAAAGAAGAAAAGAGTATAGGATCTGATGATACAAATATTTTAAGTGCACAAAAT 4200
1381 Y  G  K  E  E  K  S  I  G  S  D  D  T  N  I  L  S  A  C  N  1400
```

TABLE 1-continued

Nucleotide and Deduced
Amino Acid Sequence of the Carbamoyl Phosphate
Synthetase II Gene from *Plasmodium falciparum* [SEQ ID NOS:1 and 2]

```
4201 TCAAATAATAACTTTTCATGTAATAATGAGAATATGAATAAAGCAAACGTTGATGTTAAT 4260
1401 S   N   N   N   F   S   C   N   N   E   N   M   N   K   A   N   V   D   V   N   1420

4261 GTACTAGAAAATGATACGAAAAAACGAGAAGATATAAATACTACAACAGTATTTATGGAA 4320
1421 V   L   E   N   D   T   K   K   R   E   D   I   N   T   T   T   V   F   N   E   1440

4321 GGTCAAAATAGTGTTATTAATAATAAGAATAAAGAGAATAGTTCTTTATTGAAAGGTGAT 4380
1441 G   Q   N   S   V   I   N   N   K   N   K   E   N   S   S   L   L   K   G   D   1460

4381 GAAGAAGATATTGTGATGGTAAATTTAAAAAAGGAAAATAATTATAATAGTGTAATTAAT 4440
1461 E   E   D   I   V   N   V   N   L   K   K   E   N   N   Y   N   S   V   Y   N   1480

4441 AATGTAGATTGTAGGAAAAAGGATATGGATGGAAAAAATATAAATGATGAATGTAAAACA 4500
1481 N   V   D   C   R   K   K   D   M   D   G   K   N   I   N   D   E   C   K   T   1500

4501 TATAAGAAAAATAAATATAAAGATATGGGATTAAATAATAATATAGTAGATGAGTTATCC 4560
1501 Y   K   K   N   K   Y   K   D   M   G   L   N   N   N   I   V   D   E   L   S   1520

4561 AATGGAACATCACATTCAACTAATGATCATTTATATTTAGATAATTTTAATACATCAGAT 4620
1521 N   G   T   S   H   S   T   N   D   H   L   Y   L   D   N   F   N   T   S   D   1540

4621 GAAGAAATAGGGAATAATAAAAATATGGATATGTATTTATCTAAGGAAAAAAGTATATCT 4680
1541 E   E   I   G   N   N   K   N   M   D   M   Y   L   S   K   E   K   S   I   S   1560

4681 AATAAAAACCCTGGTAATTCTTATTATGTTGTAGATTCCGTATATAATAATGAATACAAA 4740
1561 N   K   N   P   G   N   S   Y   Y   V   V   D   S   V   Y   N   N   E   Y   K   1580

4741 ATTAATAAGATGAAAGAGTTAATAGATAACGAAAATTTAAATGATGAATATAATAATAAT 4800
1581 I   N   K   M   K   E   L   I   D   N   E   N   L   N   D   E   Y   N   N   N   1600

4801 GTTAATATGAATTGTTCTAATTATAATAATGCTAGTGCATTTGTAAATGGAAAGGATAGA 4860
1601 V   N   M   N   C   S   N   Y   N   N   A   S   A   F   V   N   G   K   D   K   1620

4861 AATGATAATTTAGAAAATGATTGTATTGAAAAAAATATGGATCATACATACAAACATTAT 4920
1621 N   D   N   L   E   N   D   C   I   E   K   N   M   D   H   T   Y   K   H   Y   1640

4921 AATCGTTTAAACAATCGTAGAAGTACAAATGAGAGGATGATGCTTATGGTAAACAATGAA 4980
1641 N   R   L   N   N   R   R   S   T   N   E   R   M   M   L   M   V   N   N   E   1660

4981 AAAGAGAGCAATCATGAGAAGGGCCATAGAAGAAATGGTTTAAATAAAAAAAATAAGAA  5040
1661 K   E   S   N   H   E   K   C   H   R   R   N   G   L   N   K   K   N   E   1680

5041 AAAAATATGGAAAAAAATAAGGGAAAAAATAAAGACAAAAGAATTATCATTATGTTAAT  5100
1681 K   N   M   E   K   N   K   G   K   N   K   D   K   K   N   Y   H   Y   V   N   1700

5101 CATAAAAGGAATAATGAATATAATAGTAACAATATTGAATCGAAGTTTAATAATTATGTT 5160
1701 H   K   R   N   N   E   Y   N   S   N   N   I   E   S   K   F   N   N   Y   V   1720

5161 GATGATATAAATAAAAAAGAATATATGAAGATGAAAATGATATATATTATTTTACACAT 5220
1721 D   D   I   N   K   K   E   Y   Y   E   D   E   N   D   I   Y   Y   F   T   H   1740

5221 TCGTCACAAGGTAACAATGACGATTTAAGTAATGATAATTATTTAAGTAGTGAAGAATTG 5280
1741 S   S   Q   G   N   N   D   D   L   S   N   D   N   Y   L   S   S   E   E   L   1760

5281 AATACTGATGAGTATGATGATGATTATTATTATGATGAACATGAAGAAGATGACTATGAC 5340
1761 N   T   D   E   Y   D   D   D   Y   Y   Y   D   E   E   E   D   D   Y   D   1780
```

TABLE 1-continued

Nucleotide and Deduced
Amino Acid Sequence of the Carbamoyl Phosphate
Synthetase II Gene from *Plasmodium falciparum* [SEQ ID NOS:1 and 2]

```
5341 GATGATAATGATGATGATGATGATGATGATGATGGGGAGGATGAGGAGGATAATGAT 5400
1781  D   D   N   D   D   D   D   D   D   D   D   G   E   D   E   E   D   N   D   1800

5401 TATTATAATGATGATGGTTATGATAGCTATAATTCTTTATCATCTTCAAGAATATCAGAT 5460
1801  Y   Y   N   D   D   G   Y   D   S   Y   N   S   L   S   S   S   R   I   S   D  1820

5461 GTATCATCTGTTATATATTCAGGGAACGAAAATATATTTAATGAAAAATATAATGATATA 5520
1821  V   S   S   V   I   Y   S   G   N   E   N   T   F   N   E   K   Y   N   D   I  1840

5521 GGTTTTAAAATAATCGATAATAGGAATGAAAAAGAGAAAGAGAAAAAGAAATGTTTTATT 5580
1841  G   F   K   I   I   D   N   R   N   E   K   E   K   E   K   K   K   C   F   I  1860

5581 GTATTAGGTTGTGGTTGTTATCGTATTGGTAGTTCTGTAGAATTTGATTGGAGTGCTATA 5640
1861  V   L   G   C   G   C   Y   R   I   Q   S   S   V   E   F   D   W   S   A   I  1880

5641 CATTGTGTAAAGACCATAAGAAAATTAAACCATAAAGCTATATTAATAAATTGTAACCCA 5700
1881  H   C   V   K   T   I   R   K   L   N   H   K   A   I   L   T   N   C   N   F  1900

5701 GAAACTGTAAGTACAGATTATGATGAAAGTGATCGTCTATATTTTGATGAAATAACAACA 5760
1901  E   T   V   S   T   D   Y   D   E   S   D   R   L   Y   F   D   E   I   T   T  1920

5761 GAAGTTATAAAATTTATATATAACTTTGAAAATAGTAATGGTGTGATTATAGCTTTTGGT 5820
1921  E   V   I   K   F   I   Y   N   F   E   N   S   N   G   V   I   I   A   F   G  1940

5821 GGACAAACATCAAATAATTTAGTATTTAGTTTATATAAAAATAATGTAAATATATTACGA 5880
1941  G   Q   T   S   N   N   L   V   F   S   L   Y   K   N   N   V   N   I   L   G  1960

5881 TCAGTGCACAAAGTGTTGATTCTTGTGAAAATAGGAATAAATTTTCGCACTTATGTGATT 5940
1961  S   V   H   K   V   L   I   V   V   K   I   G   N   F   R   T   Y   V   I  1980

5941 CTTAAAATTGATCAACCGAAATGGAATAAATTTACAAAATTATCCAAGGCTATACAATTT 6000
1981  L   K   I   D   Q   P   K   W   N   K   F   T   K   L   S   K   A   I   Q   F  2000

6001 GCTAATGAGGTAAAATTTCCTGTATTAGTAAGACCATCGTATGTATTATCTGGTGCAGCT 6060
2001  A   N   E   V   K   F   F   V   L   V   R   P   S   Y   V   L   S   G   A   A  2020

6061 ATGAGAGTTGTAAATTGTTTTGAAGAATTAAAAAACTTTTTAATGAAGGCAGCTATTGTT 6120
2021  M   R   V   V   N   C   F   E   E   L   K   N   F   L   M   K   A   A   I   V  2040

6121 AGTAAAGATAATCCTGTTCTAATATCAAAATTTATTGAGAATGCTAAAGAAATAGAAATA 6180
2041  S   K   D   N   P   V   V   I   S   K   F   T   E   N   A   K   E   I   E   I  2060

6181 GATTGTGTTAGTAAAAATGGTAAAATAATTAATTATGCTATATCTGAACATGTTGAAAAT 6240
2061  D   C   V   S   K   N   G   K   I   I   N   Y   A   I   S   E   H   V   E   N  2080

6241 CCTGGTGTACATTCAGGTGATCCAACATTAATATTACCTGCACAAAATATATATGTTGAA 6300
2081  A   G   V   H   S   C   D   A   T   L   I   L   P   A   Q   N   I   Y   V   E  2100

6301 ACACATAGGAAAATAAAGAAAATATCCGAAAACATTTCAAAATCATTAAATATATCTGGT 6360
2101  T   H   R   K   I   K   K   I   S   E   K   I   S   K   S   L   N   I   S   G  2120

6361 CCATTTAATATACAATTTATATCTCATCAAAATGAAATAAAAATTATTGAATGTAATTTA 6420
2121  P   F   N   I   Q   F   I   C   H   Q   N   E   I   K   I   I   E   C   N   L  2140

6421 AGAGCATCTAGAACTTTTCCATTTATATCAAAAGCTCTAAATCTAAACTTTATAGATTTA 6480
2141  R   A   S   R   T   F   P   F   I   S   K   A   L   N   L   N   F   I   D   L  2160
```

TABLE 1-continued

Nucleotide and Deduced
Amino Acid Sequence of the Carbamoyl Phosphate
Synthetase II Gene from Plasmodium falciparum [SEQ ID NOS:1 and 2]

```
6481 GCTACAAGGATATTAATGGGTTATGACGTCAAACCAATTAATATATCATTAATTGATTTA 6540
2161 A   T   R   I   L   N   G   Y   D   V   K   P   I   N   I   S   L   I   D   L   2180

6541 GAATATACAGCTGTAAAAGCACCGATTTTCTCATTTAATAGATTACATGGATCAGATTGT 6600
2181 E   Y   T   A   V   K   A   P   I   F   S   F   N   R   L   H   G   S   D   C   2200

6601 ATACTAGGTGTAGAAATGAAATCTACAGGTGAAGTAGCATGTTTTGGTTTAAATAAATAT 6660
2201 I   L   C   V   E   M   K   S   T   G   E   V   A   C   F   G   L   N   K   Y   2220

6661 GAAGCTTTATTAAAATCATTAATAGCTACAGGTATGAAGTTACCCAAAAAATCAATACTT 6720
2221 E   A   L   L   K   S   L   I   A   T   G   M   K   L   F   K   K   S   I   L   2240

6721 ATAAGTATTAAAAATTTAAATAATAAATTAGCTTTTGAAGAACCGTTCCAATTATTATTT 6780
2241 I   S   I   K   N   L   N   N   K   L   A   F   E   E   P   F   C   L   L   F   2260

6781 TTAATGGGATTTACAATATATGCGACTCAAGGTACGTATCATTTCTACTCTAAATTTTTA 6840
2261 L   N   G   F   T   I   Y   A   T   E   G   T   Y   D   F   Y   S   K   F   L   2280

6841 CAATCTTTTAATCTTAATAAAGGTTCTAAATTTCATCAAACACTTATTAAAGTTCATAAT 6900
2281 E   S   F   N   V   N   K   G   S   K   F   H   Q   R   L   I   K   V   H   N   2300

6901 AAAAATGCAGAAAATATATCACCAAATACAACAGATTTAATTATGAATCATAAAGTTGAA 6960
2301 K   N   A   E   N   I   S   P   N   T   T   D   L   I   M   N   H   K   V   E   2320

6961 ATGGTTATTAATATAACTGATACATTAAAAACAAAGGTTAGTTCAAATGGTTATAAAATT 7020
2321 M   V   I   N   I   T   D   T   L   K   T   K   V   S   S   N   G   Y   K   I   2340

7021 AGAAGATTAGCATCAGATTTCCAGGTTCCTTTAATAACTAATATGAAACTTTGTTCTCTT 7080
2341 R   R   L   A   S   D   F   Q   V   P   L   I   T   N   M   K   L   C   S   L   2360

7081 TTTATTGACTCATTATATAGAAAATTCTCAAGACAAAAGGAAAGAAAATCATTCTATACC 7140
2361 F   I   D   S   L   Y   R   K   F   S   R   Q   K   E   R   K   S   F   Y   T   2380

7141 ATAAAGAGTTATGACGAATATATAAGTTTGGTATAA                         7176
2381 I   K   S   Y   D   E   Y   I   S   L   V   *                2392

7177 GCAAGAAATTATTCAATAAATTCGATTTAACATTACTTATTTATGTATTTATTAACTTTC 7235

7237 ATTCCATAACAACATGAAAAGTATAAATATATAAATAGTAATATATAATATATAATATAT 7296

7297 ATATATATATATATATATATTTATTTATTTAATTATATTTACGTTTAAATATTAATAA   7356

7357 ATGTTTTTATTAAATATGATCATTAATTTATATTGATTTATTTTTTTATAAATTTTTGTT 7416

7417 ATATATACAAATTTTATTTATTCACTCATATGTATAAACCAAAATGGTTTTTTCAATTTA 7476

7477 CAAATAATTTTATAATTTTAATAAATTTATTAATTATAAAAAAAATAAAAATATATAAAC 7536

7537 ATTAAAATGTATAAATTCTTTTAATTATATAATAATTTATAAATGTTATGATTTTTTTAA 7596
```

TABLE 1-continued

Nucleotide and Deduced
Amino Acid Sequence of the Carbamoyl Phosphate
Synthetase II Gene from Plasmodium falciparum [SEQ ID NOS:1 and 2]

```
7597 AAAATTCAACGAAAAAAAAGAGGAACTGTATATACAAAAGGGACTATATATATGTATATA 7656

7657 TATATATATATATATATGTTTTTTTTTCCTTATTCTAGA                       7695
```

The GAT domain is made up of two subdomains: a putative structural domain (1–750) and a glutaminase domain (1447–2070). These two subdomains are separated by a first inserted sequence (751–1446, underlined). The two ATP binding subdomains of the synthetase subunit, CPSa (2071–3762) and CPSb (5572–5173) are separated by a second inserted sequence (3763–5571, underlined).

As these inserted sequences are not found in other carbamoyl phosphate synthetase genes they represent prime targets for therapies including, but not limited to, antisense nucleotides, ribozymes and triplex forming nucleotides as there is a decreased likelihood of deleterious reaction with host homologues of the gene.

Antisense RNA molecules are known to be useful for regulating gene expression within the cell. Antisense RNA molecules which are complementary to portion(s) of CPSII can be produced from the CPSII sequence. These antisense molecules can be used as either diagnostic probes to determine whether or not the CPSII gene is present in a cell or can be used as a therapeutic to regulate expression of the CPSII gene, Antisense nucleotides prepared using the CPSII sequence include nucleotides having complementarity to the CPSII mRNA and capable of interfering with its function in vivo and genes containing CPSII sequence elements that can be just transcribed in living cells to produce antisense nucleotides. The genes may include promoter elements from messenger RNA (polymerase II) from cells, viruses, pathogens or structural RNA genes (polymerase I & III) or synthetic promoter elements. A review of antisense design is provided in "Gene Regulation; Biology of Antisense RNA and DNA" R. P. Erickson and J. G. Izant, Raven Press 1992. Reference may also be had to U.S. Pat. No. 5,208,149 which includes further examples on the design of antisense nucleotides. The disclosure of each of these references is incorporated herein by reference.

As used herein the term "nucleotides" include but are not limited to oligomers of all naturally-occurring deoxyribonucleotides and ribonucleotides as well as any nucleotide analogues. Nucleotide analogues encompass all compounds capable of forming sequence-specific complexes (eg duplexes or hetroduplexes) with another nucleotide including methylphosphonates or phosphorothioates but may have advantageous diffusion or stability properties. The definition of nucleotides includes natural or analogue bases linked by phosphodiester bonds, peptide bonds or any other covalent linkage. These nucleotides may be synthesised by any combination of in vivo in living cells, enzymatically in vitro or chemically.

Ribozymes useful in regulating expression of the CPSII gene include nucleotides having CPSII sequence for specificity and catalytic domains to promote the cleavage of CPSII mRNA in vitro or in vivo. The catalytic domains include hammerheads, hairpins, delta-virus elements, ribosome RNA introns and their derivatives. Further information regarding the design of ribozymes can be found in Haseloff, J. & Gerlach, W. L. (1988) Nature 334. 585; Kruger, K., Grabowski, P. J., Zaug, A. J., Sands, J., Gottschling, D. E. & Cech, T. R. (1982) Cell 31, 147; International Patent Application No. WO 88/04300, U.S. Pat. No. 4,987,071 and U.S. Pat. No. 5,254,678. The disclosure of each of these references is incorporated herein by reference. The catalytic elements may enhance the artificial regulation of a CPSII target mRNA by accelerating degradation or some other mechanism.

Triple helix oligonucleotides can be used to inhibit transcription from the genome. Given the sequence provided herein for the CPSII gene it will now be possible to design oligonucleotides which will form triplexes thereby inhibiting transcription of the CPSII gene. Information regarding the generation of oligonucleotides suitable for triplex formation can be found in a Griffin et al (Science 245:967–971 (1989)) this disclosure of this reference is incorporated herein by reference.

Triplex agents include all nucleotides capable of binding to the CPSII gene through formation of the complex with DNA or chromatin. The interaction can be through formation of a triple-stranded Hoogsteen structure or other mechanisms such as strand invasion that relies on the CPSII sequence information.

Accordingly, in a fourth aspect the present invention consists in a ribozyme capable of cleaving carbamoyl phosphate synthetase II mRNA, the ribozyme including sequences complementary to portions of mRNA obtained from the nucleic acid molecule of the first aspect of the present invention.

In a preferred embodiment of this aspect of the present invention the ribozyme includes sequences complementary to mRNA obtained from the first or second inserted sequences of the nucleic acid molecule of the first aspect of the present invention.

In a fifth aspect the present invention consists in an antisense oligonucleotide capable of blocking expression of the nucleic acid molecule of the first aspect of the present invention.

As stated above, in one aspect the present invention relates to a method of producing CPSII by recombinant technology. The protein produced by this method and the polypeptides of the present invention will be useful in in vitro drug binding studies in efforts to develop other antimalarial therapeutics.

In order that the nature of the present invention may be more clearly understood the method by which the P. falciparum CPSII gene was cloned will now be described with reference to the following Examples and Figures.

BRIEF DESCRIPTION OF THE DRAWINGS

FIG. 2: P. falciparum carbamoyl phosphate synthetase II (pfCPSII) gene sequence with the 21 consensus GUC (GTC) ribozyme cleavage sites identified (underlined) (SEQ ID NO:1).

FIG. 3: Output of RNA mfold analysis showing the GUC sites from CPSRz1/M10 a and CPSRz4/M15 more accessible than the M17 and M18 sites (Seq. Id. No:1).

FIGS. 4A–C: A. Sequences for the phosphorothioated antisense DNA used in inhibition studies of *P. Falciparum* in culture (SEQ ID NOS:3–15); B. Map of the positions of the antisense sequences within the pfCPSII gene; C. Growth supression of *P. Falciparum* in vitro after a 24 hr incubation with the oligonucleotides.

FIG. 5. Cultures of *P. Falciparum* and selected mammalian cell lines were incubated with 2.5 and 5.0 μM CPSRz1, CPSRz4 and 60-mer random oligonucleotide. Cell viability was assessed by measuring the % incorporation of tritiated hypoxanthine.

EXAMPLES

Cloning of the *P. falciparum* Carbamoyl Phosphate Synthetase II (pfCPSII) Gene

The conventional way to screen for genes of which the amino acid sequence had not been previously determined is via heterologous probing, i.e. with gene fragments of the target enzyme from closely related organisms. This has proved to be unsuccessful for several workers with *Plasmodium falciparum* largely due to the unusually high A-T content of its genome. After initial unfruitful attempts to isolate the CPSII gene in *Plasmodium falciparum* using a yeast ura2 gene fragment (Souciet et al., 1989), the present inventors opted to amplify part of the CPSII gene using the polymerase chain reaction (PCR) (Saiki et al., 1988) with a view to use the amplified product as probe for screening.

The present inventors isolated and cloned a PCR product using oligonucleotides designed from conserved sequences from the amino terminal GAT domain and the first half of the synthetase domain of the CPS gene. Nucleotide sequencing confirmed that a portion of the CPSII gene had been obtained. Total parasite DNA was fragmented with a restriction enzyme and subjected to Southern analysis using the CPSII-specific gene probe. The sizes of DNA fragments hybridizing to the gene probe were determined then the DNA in the corresponding bands were used for the construction of a "mini-library". In this way a smaller population of clones were screened for the pf CPSII gene.

To isolate the full length pfCPSII gene, a series of mini-libraries were constructed utilising different segments of known sequence to gain information of the unknown flanking regions both towards the 5' and 3' termini of the gene using "gene-walking". The strategy employed is summarised in FIG. 1.

In the first Southern analysis, total *P. falciparum* DNA was digested with HindIII and EcoRI and hybridisation was carried out using the pfCPSII 453 bp PCR product. A 3.0 kb HindIII and a smaller EcoRI fragment hybridised to the probe. Subsequent screening of a HindIII pTZ18U mini-library resulted in the isolation of a recombinant that contained a 3.0 kb pfCPSII gene fragment, CPS2. The 453 bp PCR product was localised in the middle of this segment.

Two regions from both the 5' and 3' ends of CPS2 were used to isolate neighbouring sequences at either end in order to obtain the further gene sequences. A HindIII/EcoRI fragment from the 5' end of CPS2 was instrumental in isolating a further 1.5 kb fragment, CPS1 consisting of the complete 5' region of the gene and some non-encoding sequences.

A 550 bp inverse PCR (IPCR; Triglia et al., 1988) product was obtained with the aid of known sequences from the 3' end of CPS2.

This IPCR product was used to screen for the 3' region flanking CPS2, A 3.3 kb HindIII recombinant containing CPS3 as well as a related 3.3 kb XBaI clone (not presented in FIG. 1) were isolated by the mini-library technique. Using a 200 bp XbaI/HindIII fragment from the 3' end of CPS 3, a 1.3 kb XbaI segment, CPS4 was cloned which contained the putative stop codon and some 3' non-coding region.

Combining these four gene fragments (CPS1, CPS2, CPS3 and CPS4) excluding their overlaps, gives a total of 8.8 kb consisting of approximately 7.0 kb coding and 1.8 flanking sequences.

The complete nucleotide sequence of the CPSII gene in *P. falciparum,* together with its 5' and 3' flanking sequences, is presented in Table 1.

Design of Ribozymes

Our first generation ribozymes were designed using the consensus sequences cleavage site, GUC, found in naturally occurring hammerhead ribozymes (see Haseloff and Gerlach, 1988, the entire contents of which are incorporated herein by reference). In total, there are 21 GUC sites in the entire 7.1 kb coding region of pfCPSII (FIG. 1 and Table 2). To select the putative sites that are relatively more accessible to binding, the pfCPSII mRNA folding pattern was analysed using mfold Program (ANGIS/GCG). This was done in windows of 500 nucleotides, with 250 nucleotide overlaps between each window.

To screen for the best (most accessible) sites within the CPS II mRNA, a series of antisense DNA oligonucleotides were designed and synthesised from sequences around the selected (by mfold) GUC sequences mentioned above. Also included were two antisense oligonucleotides (M17 and M18) where the mfold program had indicated intramolecular base pairing of the GUC sequences may be occurring (FIG. 2). As seen from the bio-assays of suppression of malarial growth by the antisense oligonucleotides, there appears to be a correlation between the predicted accessibility of each site and the effectiveness as judged by the % inhibition of growth (FIG. 3). The antisense oligonucleotides M10 (Rz1 site) and M15 (Rz4 site) were much more effective in growth inhibition than M17 and M18 where the mfold program predicted internal base pairing.

These results led to the synthesis of ribozymes based on the Rz1 and Rz4 sites (ribozymes CPSRz1 and CPSRz4).

TABLE 2

GUC sites present in the coding region of pfCPSII. Nucleotide numbers indicate the position of the G of the triplet in the gene sequence.

| | | |
|---|---|---|
| 1. | 170 | |
| 2. | 281 | |
| 3. | 380 | |
| 4. | 905 | CPSRz1 site/M10 |
| 5. | 1294 | |
| 6. | 1306 | |
| 7. | 1607 | |
| 8. | 1939 | |
| 9. | 1967 | |
| 10. | 2324 | |
| 11. | 2387 | |
| 12. | 3195 | |
| 13. | 3731 | CPSRz4 site/M15 |
| 14. | 3817 | |
| 15. | 3823 | |
| 16. | 4013 | |
| 17. | 432Z | |
| 18. | 5223 | M17 |
| 19. | 5735 | |
| 20. | 6359 | |
| 21. | 6383 | |

CPSRz1 and CPSRz4 as Antimalarials

The ability of CPSRz1 and CPSRz4 to cleave a 550 base mRNA fragment of pfCPSII was assessed. Growth inhibition studies on *P. falciparum* cultures were initially conducted using higher concentrations of ribozymes, at 2.5 and 5.0 μM. Both ribozymes were shown to be very effective at these concentrations as shown in the marked decrease in incorporation of tritiated hypoxanthine (FIG. 4). In the same study, a series of mammalian cell lines in culture were treated with the same concentrations of the ribozymes, and no effect cell viability was observed. As a negative control, a 60-mer DNA oligonucleotide of random sequence was used.

Figure 1:
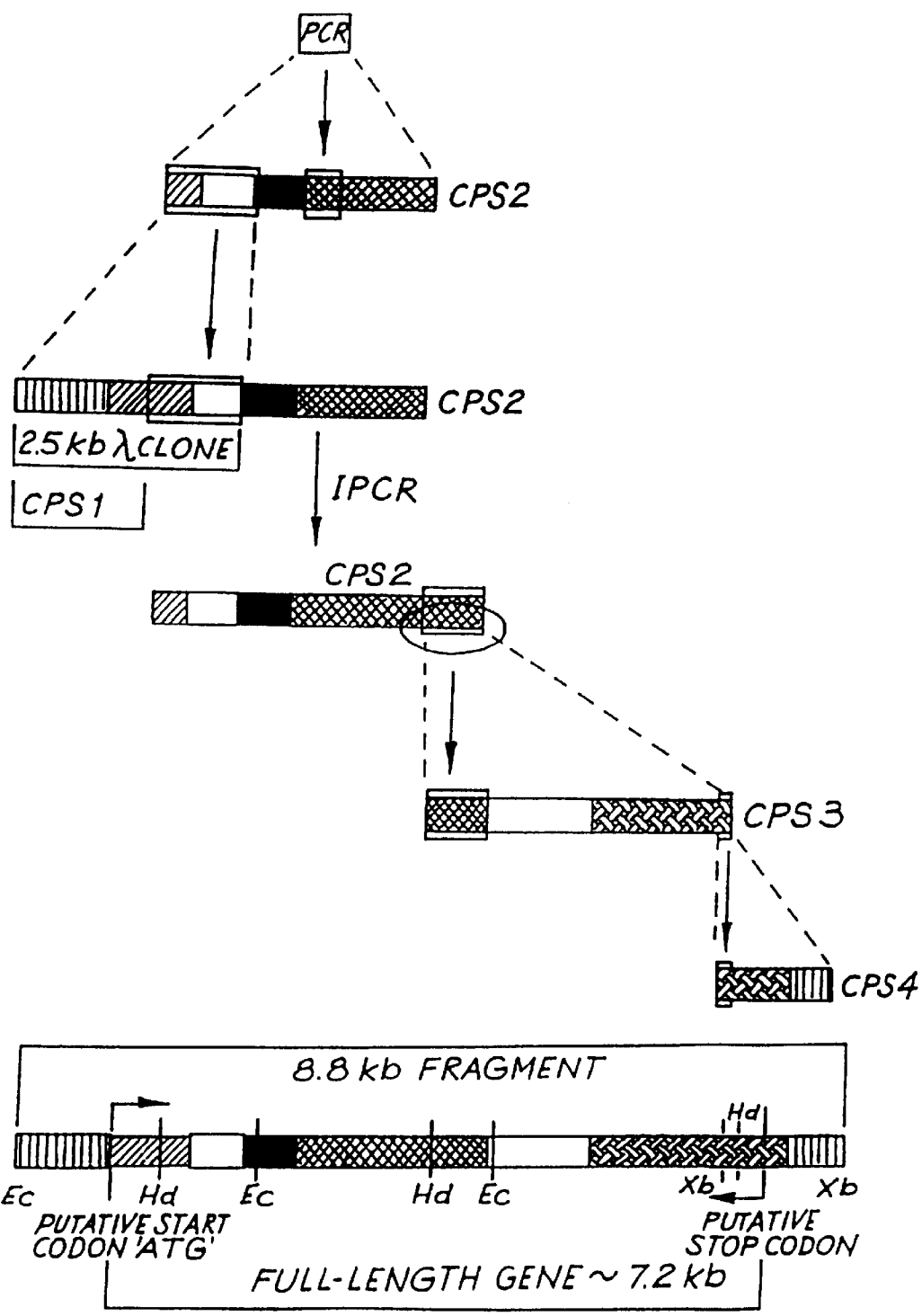
FIG. 1: A summary of a "gene walking" strategy used to clone and sequence the full length P. falciparum carbamoyl phosphate synthetase II gene.
Figure 5:
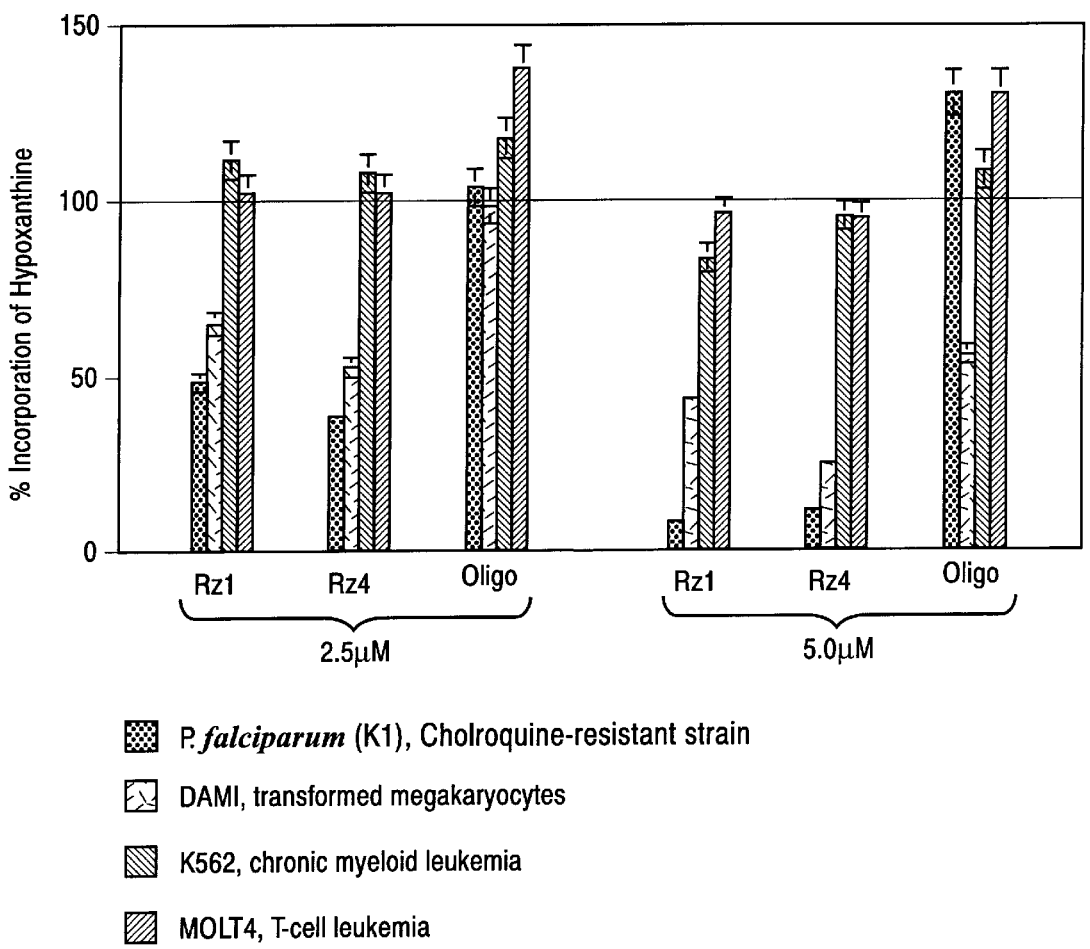

As will be readily appreciated by those skilled in the art the isolation of this gene and its sequencing by the present inventors opens up a range of new avenues for treatment of *Plasmodium falciparum* infection. The present invention enables the production of quantities of the *Plasmodium falciparum* carbamoyl phosphate synthetase II enzyme using recombinant DNA technology. Characterisation of this enzyme may enable its use as a chemotherapeutic loci.

The isolation of this gene also will enable the production of antisense molecules, ribozymes or other gene inactivation agents which can be used to prevent the multiplication of the parasite in infected individuals.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Cox, F. E. G. (1991) Malaria vaccines: while we are waiting. Parasitology Today 7: 189–190

Gero, A. M. and O'Sullivan, W. J. (199)) Purines and pyrimidines in malarial parasites. Blood Cells 16: 467–498

Hammond, D. J. Burchell, J. R. and Pudney, M. (1965) Inhibition of pyrimidine biosynthesis de novo in Plasmodium falciparum by 2.(4.t-butylcyclohexyl)-3-hydroxy-1, 4-naphthoquinine in vitro. Mol. Biochem. Parasitol 14: 97–109

Haseloff, J. And Gerlach, W. L. (1988) Simple RNA enzymes with new and highly specific endoribonuclease activity. Nature 334:585–591

Hill, B., Kilsby, J. Rogerson, G. W., McIntosh, R T. and Ginger, C. D. (1981). The Enzymes of pyrimidine biosynthesis in a range of parasitic protozoa and helminths. Mol. Biochem. Parasitol. Z: 123–134.

Johnson, C. Malaria back to plague us. Sydney Morning Herald, Nov. 13, 1991.

Jones, M. E. (1980) Pyrimidine nucleotide biosynthesis in animals: genes, enzymes and regulation of UMP biosynthesis. Annu. Rev. Biochem. 49: 253–279.

Krungkrai, J. Cerami, A. and Henderson, G. B. (1990) Pyrimidine biosynthesis in parasitic protozoa: purification of a monofunctional dihydroorotase from Plasmodium berghei and Crithidia fasciculata. Biochemistry 29: 6270–6275.

Krungkrai, J. Krungkrai, S. R. and Phakanont, K. (1992) Antimalarial activity of orotate analogs that inhibit dihydrootase and dihydroorotate dehydrogenase. Biochem. Pharmacol. 43: 1295–1301.

Marshal, E. (1991) Malaria parasite gaining ground against science. Science 2: 190, Nyunoya, H., Broglie, K. E., Widgren, W. E. and Lusty C. J (1985) Characterization and derivation of the gene coding for mitochondrial carbamyl phosphate synthetase I of rat. J. Biol. Chem. 260: 9346–9356.

Prapunwattana, P., O'Sullivan, W. J. and Yuthavong, Y. (1988) Depression of Plasmodium falciparum dihydroorotate dehydrogenase activity in in vitro culture by tetracycline. Mol. Biochemi. 27: 119–124.

Queen, S. A., Vander Jagt, D. L. and Reyes, P. (1990) In vitro susceptibilities of Plasmodium falciparum to compounds which inhibit nucleotide metabolism. Antimicrob. Agents Chemother. 34: 1393–1398.

Reyes, P., Rathod, P. K., Sanchez, D. J. Mrema, J. E. K., Rieckmann, K. H. and Heidrich, H. G. (1982) Enzymes of purine and pyrimidine metabolism from the human malaria parasite, Plasmodium falciparum. Mol. Biochem. Parasitol. 5: 275–290.

Rubino S. D., Nyunoya, H. and Lusty, C. J. (1986) JBC 261(24):11320–11327.

Saiki, R. K., Gelfand, D. H., Stoffel, S., Scharf, S. J., Higuchi, R., Horn, G. T., Mullis K. B. and Erlich H. A. (1958) Science 239:487–491, Scott, H. V., Gero, A. M. and O'Sullivan, W. J. (1986) In vitro inhibition of Plasmodium falciparum by pyrazofurin, an inhibitor of pyrimidine biosynthesis de novo. Mol Biochem. Parasitol. 18: 3–15.

Sherman, I. W. (1979) Biochemistry of Plasmodium (malarial parasites) Microbiol. Rev. 43: 453–495.

Simmer, J. P., Kelly, R. E., Rinker, Jr., A. G., Scully, J. L. and Evans D. R. (1990) Mammalian carbamyl phosphate synthetase (CPS), J. Biol. Chem 265: 10395–10402.

Simmer, J. P., Kelly, R. E., Austin, G. R., Jr., Scully, J. L. and Evans, D. R. (1990) JBC 285(18):10395–10402.

Souciet, J. L., Nagy, M., Le Gouar, M., Lacroute, F. and Potier, S. (1989) Gene (Amst.) 79: 59–70.

Triglia, T., Peterson, M. G. and Kemp, D. J. (1988) PNAS 16:8186.

Werner, M., Feller, A. and Pierard, A. (1985) Nucleotide sequence of yeast genie CPA1 encoding the small subunit of arginine-pathway carbamoyl-phosphate synthetase. Eur. J. Biochem. 146: 371–381.

What is claimed is:

1. A ribozyme capable of cleaving carbamoyl phosphate synthetase II mRNA, the ribozyme including sequences complementary to portions of mRNA obtained from the nucleic acid molecule as shown in SEQ ID NO:1.

2. The ribozyme as claimed in claim 1 in which the ribozyme includes sequences complementary to portions of mRNA obtained from inserted sequence one or two of the nucleic acid molecule as shown by nucleotides 1976–2671 or 4988–6796 of SEQ. ID. NO: 1.

3. An antisense oligonucleotide capable of blocking expression of the nucleic acid molecule as shown in SEQ ID No:1.

4. A polynucleotide construct which produces in a cell the ribozyme as claimed in claim 1 or the antisense oligonucleotide as claimed in claim 3.

* * * * *

SEQUENCE LISTING

```
<160> NUMBER OF SEQ ID NOS: 15

<210> SEQ ID NO 1
<211> LENGTH: 8920
<212> TYPE: DNA
<213> ORGANISM: Plasmodium falciparum

<400> SEQUENCE: 1
```

-continued

| | | | | |
|---|---|---|---|---|
| gaattccttc | agccaaaaaa | aatgacaacg | caaattttaa | gaaagagaaaa acaatcgact | 60 |
| cgtctttgaa | tgaggttaga | aattcgatac | gtgaaaggga | cttaagaagg cttaacagag | 120 |
| aaaagagtaa | aatcttataa | gcatttgaag | gaaaaaataa | taaataaaaa aaataaaaag | 180 |
| ataaaaaata | tttatatttg | atatgtagta | tatataatga | ttattcatat taataacata | 240 |
| gataaaaaac | tttttttttt | ttttttttc | tttatattta | ttaacaatac atttaagtta | 300 |
| ttttatatat | atatatatat | atatatatat | atatatatat | atatatgttt gtgtgttcat | 360 |
| ttgtttataa | aattacttga | aatataaaac | ttattaatat | atttccaatt aatatgaata | 420 |
| caattattaa | tattttgatg | tgtacacatt | aatatagttt | tacacttctt ataataaaac | 480 |
| catcctatat | attatacaca | atatataata | ctccccaata | ttgtggttcc tataatttta | 540 |
| tttatatatt | tatttattaa | tttattcatt | tatttatttt | ttttcttagt ttataaaata | 600 |
| gtaattctac | taatttaaaa | aaaaaaaaaa | aaaaaaaaaa | aaaagaaaa aaaaaaaatt | 660 |
| tacatatgaa | aaatgaactt | gtatatgtaa | atttataaat | atttttaaaca taaatataaa | 720 |
| tgtataaaaa | aaaaaaagaa | aatgggaaa | aaataatata | gatatatata taaatatata | 780 |
| tatatatata | attattgggg | atattctctg | aatcataggt | cttaaacagt tttattcttt | 840 |
| taacatcaca | aagttgttat | taaaagtata | tatatcttat | tggttcctat ataaaactat | 900 |
| agtattctat | aatatattct | gtatatttca | ttttatcatt | tgtaagcaat ccctattat | 960 |
| tataattatt | atttttttttt | ttataaaaga | ggtataaaac | agtttattca attttttttcc | 1020 |
| taaaggagca | accttcagtc | aatttacatt | ttccaccggt | tggttggcac aacataatgt | 1080 |
| tacagctaaa | aaaagaaaga | aaaaaaaaaa | aaaaaaaaaa | aaaaaaaaaa atatatatat | 1140 |
| atatatatat | atatacataa | tatgtacaat | gctaccatac | aagtatataa attttttcaac | 1200 |
| attgttgtga | tgttgcattt | ttcttatgta | tatttcttttt | aaatataatt tatatatata | 1260 |
| tatatatata | tatatatata | tatttgttct | tatagatttt | aaaacagttg ggaggttaat | 1320 |
| tcttgaagat | ggtaacgaat | ttgtagggta | cagtgtaggt | tacgaagggt gtaaaggaaa | 1380 |
| taatagtata | tcatgtcata | aggagtatag | aaatatattat | aataatgata atagcaagaa | 1440 |
| tagtaataat | tcattttgta | ataatgaaga | aaacaatttg | aaagatgatt tattatataa | 1500 |
| aaatagtcga | ttagaaaatg | aagatttttat | tgttacaggt | gaagttatat ttaatacagc | 1560 |
| tatggttgga | tatcctgaag | ctttaacgga | cccaagttat | tttggtcaaa tattagtttt | 1620 |
| aacatttcct | tctattggta | attatggtat | tgaaaaagta | aaacatgatg aaacgtttgg | 1680 |
| attagtacaa | aattttgaaa | gtaataaaat | tcaagtacaa | ggtttagtta tttgtgaata | 1740 |
| ttcgaagcaa | tcatatcatt | acaattctta | tattaccttta | agtgaatggt taagagattta | 1800 |
| taaaattcca | tgtataggtg | gtatagatac | aagagcctta | acaaaacttttt taagagaaaa | 1860 |
| aggtagtatg | ttaggtaaaa | tagttatata | taaaaacaga | caacatatta ataaattata | 1920 |
| taaagaaatt | aatctttttg | atcctggtaa | tatagatact | ctaaaatatg tatgtaatca | 1980 |
| ttttatacgt | gttattaagt | tgaataatat | tacatataat | tataaaaata ggaagaatt | 2040 |
| taattatacc | aatgaaatga | ttactaatga | ttcttcaatg | gaagatcatg ataatgaaat | 2100 |
| taatggtagt | atttctaatt | ttaataattg | tccaagtatc | tctagttttg ataaaagtga | 2160 |
| atcgaaaaat | gttattaatc | atacattgtt | aagagataaa | atgaacctaa taacttcatc | 2220 |
| tgaagaaaat | ctgaaagatc | ttcataattg | taatttttagt | aatagtagtg ataaaaatga | 2280 |
| ttctttttttt | aagttatatg | gtatatgtga | atatgataaa | tatttaattg accttgaaga | 2340 |
| aaatgctagc | tttcattata | ataatgtaga | tgaatatgga | tattatgatg ttaataaaaa | 2400 |

```
tacaaatatt ctatctaata ataaaataga acaaaacaac aataacgaaa ataacaaaaa    2460
taacaaaaat aacaacaata acgaggttga ttatataaag aaagatgagg ataataatgt    2520
caatagtaag gtcttttata gccaatataa taataatgca caaaataatg aacataccga    2580
atttaattta aataatgatt attctactta tattagaaag aaaatgaaaa atgaagaatt    2640
ccttaatttg gtaaacaaaa gaaaagtaga ccataaagaa aaaattattg ttattgttga    2700
ttgtggtatt aaaaatagta taatcaaaaa tttaataaga cacggtatgg atcttccatt    2760
aacatatatt attgtacctt attattacaa ttttaatcat atagattatg atgcagttct    2820
tttatctaat ggtcctggag atcctaaaaa gtgtgatttc cttataaaaa atttgaaaga    2880
tagtttaaca aaaaataaaa ttatatttgg tatttgttta ggtaatcaac tattaggtat    2940
atcattaggt tgtgacacat ataaaatgaa atatggtaat agaggtgtta atcaacccgt    3000
aatacaatta gtagataata tatgttacat tacctcacaa aatcatggat actgtttaaa    3060
gaaaaaatca attttaaaaa gaaagagct tgcgattagt tatataaatg ctaatgataa    3120
atctatagaa ggtatttcac ataaaaatgg aagattttat agtgtccagt ttcatcctga    3180
gggtaataat ggtcctgaag atacatcatt tttatttaag aattttcttt tagatatctt    3240
taataagaaa aaacaatata gagaatattt aggatataat attatttata taaaaaagaa    3300
agtgcttctt ttaggtagtg gtggtttatg tataggacaa gcaggagaat tcgattattc    3360
aggaacacaa gcaattaaaa gtttaaaaga atgtggtata tatgttatat tagttaatcc    3420
taacatagca actgttcaaa catcaaaagg tttggcagat aaggtatact ttttaccagt    3480
taattgtgaa tttgtagaaa aaattattaa aaaggaaaaa cctgattta ttttatgtac    3540 atttggtggt cagacagctt taaattgtgc tttaatgtta gatcaaaaaa aagtattgaa    3600
aaagaataat tgtcaatgtt taggtacatc tttagaatct ataagaataa cagaaaatag    3660
aacattattt gctgaaaaat taaagaaat taatgaaaga atagctccat atggtagtgc    3720
aaaaaatgtt aatcaagcta ttgatatagc taataaaata ggatatccaa tattagtacg    3780
tacaacattt tcgttaggag gattaaatag tagtttcata aataatgaag aagaacttat    3840
cgaaaaatgt aataaaatat ttttacaaac tgataatgaa atatttatag ataaatcatt    3900
acaaggatgg aaagaaatag aatatgaatt attaagagat aataaaaata attgtatagc    3960
tatatgtaat atggaaaata tagatccatt aggtatacat acaggagata gtatagttgt    4020
tgcaccttca caaacattaa gtaattatga atattataaa tttagagaaa tagcattaaa    4080
ggtaattaca catttaaata ttataggaga atgtaatata caatttggta taaatccaca    4140
aacaggagaa tattgtatta ttgaagttaa tgctaggctt agtagaagtt cagcattagc    4200
ttctaaagct actggttatc cacttgctta tatatcagca aaaatagcct tgggatatga    4260
tttgataagt ttaaaaaata gcataactaa aaaaacaact gcctgttttg aaccctctct    4320
agattacatt acaacaaaaa taccacgatg ggatttaaat aaatttgagt ttgcttctaa    4380
tacaatgaat agtagtatga aaagtgtagg agaagttatg tctataggta gaacctttga    4440
agaatctata caaaaatctt taagatgtat tgatgataat tatttaggat ttagtaatac    4500
gtattgtata gattgggatg aaaagaaaat tattgaagaa ttaaaaaatc catcaccaaa    4560
aagaattgat gctatacatc aagctttcca tttaaatatg cctatggata aaatacatga    4620
gctgacacat attgattatt ggttcttaca taaattttat aatatatata atttacaaaa    4680
taagttgaaa acgttaaaat tagagcaatt atctttaat gatttgaagt attttaagaa    4740
```

```
gcatggtttt agtgataagc aaatagctca ctacttatcc ttcaacacaa gcgataataa   4800
taataataat aataatatta gctcatgtag ggttacagaa aatgatgtta tgaaatatag   4860
agaaaagcta ggattatttc cacatattaa agttattgat accttatcag ccgaatttcc   4920
ggctttaact aattatttat atttaactta tcaaggtcaa gaacatgatg ttctcccatt   4980
aaatatgaaa aggaaaaaga tatgcacgct taataataaa cgaaatgcaa ataagaaaaa   5040
agtccatgtc aagaaccact tatataatga agtagttgat gataaggata cacaattaca   5100
caaagaaaat aataataata ataatatgaa ttctggaaat gtagaaaata aatgtaaatt   5160
gaataaagaa tcctatggct ataataattc ttctaattgt atcaatacaa ataatattaa   5220
tatagaaaat aatatttgtc atgatatatc tataaacaaa aatataaaag ttacaataaa   5280
caattccaat aattctatat cgaataatga aatgttgaa acaaacttaa attgtgtatc    5340
tgaaagggcc ggtagccatc atatatatgg taaagaagaa aagagtatag gatctgatga   5400
tacaaatatt ttaagtgcac aaaattcaaa taataacttt tcatgtaata atgagaatat   5460
gaataaagca aacgttgatg ttaatgtact agaaaatgat acgaaaaaac gagaagatat   5520
aaatactaca acagtatttta tggaaggtca aaatagtgtt attaataata agaataaaga   5580
gaatagttct ttattgaaag gtgatgaaga agatattgtg atggtaaatt taaaaaagga   5640
aaataattat aatagtgtaa ttaataatgt agattgtagg aaaaaggata tggatggaaa   5700
aaatataaat gatgaatgta aaacatataa gaaaaataaa tataagata tgggattaaa    5760
taataatata gtagatgagt tatccaatgg aacatcacat tcaactaatg atcatttata   5820
tttagataat tttaatacat cagatgaaga aatagggaat aataaaaata tggatatgta   5880
tttatctaag gaaaaaagta tatctaataa aaaccctggt aattcttatt atgttgtaga   5940
ttccgtatat aataatgaat acaaaattaa taagatgaaa gagttaatag ataacgaaaa   6000
tttaaatgat gaatataata ataatgttaa tatgaattgt tctaattata ataatgctag   6060
tgcatttgta aatggaaagg atagaaatga taatttagaa aatgattgta ttgaaaaaaa   6120
tatggatcat acatacaaac attataatcg tttaaacaat cgtagaagta caaatgagag   6180
gatgatgctt atggtaaaca atgaaaaaga gagcaatcat gagaagggcc atagaagaaa   6240
tggtttaaat aaaaaaaata agaaaaaaaa tatggaaaaa aataagggaa aaaataaaga   6300
caaaaagaat tatcattatg ttaatcataa aaggaataat gaatataata gtaacaatat   6360
tgaatcgaag tttaataatt atgttgatga tataaataaa aagaatatt atgaagatga    6420
aaatgatata tattatttta cacattcgtc acaaggtaac aatgacgatt taagtaatga   6480
taattatttta agtagtgaag aattgaatac tgatgagtat gatgatgatt attattatga   6540
tgaagatgaa gaagatgact atgacgatga taatgatgat gatgatgatg atgatgatga   6600
tggggaggat gaggaggata tgattatta taatgatgat ggttatgata gctataattc    6660
tttatcatct tcaagaatat cagatgtatc atctgttata tattcaggga cgaaaatat    6720
atttaatgaa aaatataatg atataggtttt taaaataatc gataataggga atgaaaaaga   6780
gaaagagaaa aagaaatgtt ttattgtatt aggttgtggt tgttatcgta ttggtagttc   6840
tgtagaattt gattggagtg ctatacattg tgtaaagacc ataagaaaat taaaccataa    6900
agctatatta ataaattgta acccagaaac tgtaagtaca gattatgatg aaagtgatcg   6960
tctatatttt gatgaaataa caacagaagt tataaaattt atatataact ttgaaaatag   7020
taatggtgtg attatagcatt ttggtggaca aacatcaaat aatttagtat ttagtttata   7080
taaaaataat gtaaatatat taggatcagt gcacaaagtg ttgattgttg tgaaaatagg   7140
```

-continued

```
aataaatttt cgcacttatg tgattcttaa aattgatcaa ccgaaatgga ataaatttac      7200
aaaattatcc aaggctatac aatttgctaa tgaggtaaaa tttcctgtat tagtaagacc      7260
atcgtatgta ttatctggtg cagctatgag agttgtaaat tgttttgaag aattaaaaaa      7320 cttttttaatg aaggcagcta ttgttagtaa agataatcct gttgtaatat caaaatttat    7380
tgagaatgct aaagaaatag aaatagattg tgttagtaaa aatggtaaaa taattaatta    7440
tgctatatct gaacatgttg aaaatgctgg tgtacattca ggtgatgcaa cattaatatt    7500
acctgcacaa aatatatatg ttgaaacaca taggaaaata aagaaaatat ccgaaaagat    7560
ttcaaaatca ttaaatatat ctggtccatt taatatacaa tttatatgtc atcaaaatga    7620
aataaaaatt attgaatgta atttaagagc atctagaact tttccattta tatcaaaagc    7680
tctaaatcta aactttatag atttagctac aaggatatta atgggttatg acgtcaaacc    7740
aattaatata tcattaattg atttagaata tacagctgta aaagcaccga ttttctcatt    7800
taatagatta catggatcag attgtatact aggtgtagaa atgaaatcta caggtgaagt    7860
agcatgtttt ggtttaaata aatatgaagc tttattaaaa tcattaatag ctacaggtat    7920
gaagttaccc aaaaaatcaa tacttataag tattaaaaat ttaaataata aattagcttt    7980
tgaagaaccg ttccaattat tattttttaat gggattaca atatatgcga ctgaaggtac    8040
gtatgatttc tactctaaat tttagaatc tttaatgtt aataaaggtt ctaaatttca     8100
tcaaagactt attaaagttc ataataaaaa tgcagaaaat atatcaccaa atacaacaga    8160
tttaattatg aatcataaag ttgaaatggt tattaatata actgatacat taaaaacaaa    8220
ggttagttca aatggttata aaattagaag attagcatca gatttccagg ttcctttaat    8280
aactaatatg aaactttgtt ctcttttat tgactcatta tatagaaaat tctcaagaca    8340
aaaggaaaga aaatcattct ataccataaa gagttatgac gaatatataa gtttggtata    8400
agcaagaaat tattcaataa attcgattta acattactta tttatgtatt tattaactt    8460 cattccataa caacatgaaa agtataaata tataaatagt aatatataat atataatata    8520
tatatatata tatatatata tatttatta tttaattata tttacgttta aatattaata    8580
aatgttttta ttaaatatga tcattaattt atattgattt atttttttat aaattttgt    8640 tatatataca aatttattt attcactcat atgtataaac caaaatggtt ttttcaattt    8700
acaaataatt ttataatttt aataaattta ttaattataa aaaaaataaa aatatataaa    8760
cattaaaatg tataaattct tttaattata taataattta taaatgttat gattttttta    8820
aaaaattcaa cgaaaaaaaa gaggaactgt atatacaaaa gggactatat atatgtatat    8880
atatatatat atatatatgt tttttttcc ttattctaga                          8920
```

<210> SEQ ID NO 2
<211> LENGTH: 2391
<212> TYPE: PRT
<213> ORGANISM: Artificial Sequence
<220> FEATURE:
<223> OTHER INFORMATION: Description of Artificial Sequence: protein

<400> SEQUENCE: 2

```
Met Tyr Ile Ser Phe Lys Tyr Asn Leu Tyr Ile Tyr Ile Tyr Ile Tyr
  1               5                  10                  15

Ile Tyr Ile Phe Val Leu Ile Asp Phe Lys Thr Val Gly Arg Leu Ile
             20                  25                  30

Leu Glu Asp Gly Asn Glu Phe Val Gly Tyr Ser Val Gly Tyr Glu Gly
         35                  40                  45
```

-continued

```
Cys Lys Gly Asn Asn Ser Ile Ser Cys His Lys Glu Tyr Arg Asn Ile
     50                  55                  60
Ile Asn Asn Asp Asn Ser Lys Asn Ser Asn Asn Ser Phe Cys Asn Asn
 65                  70                  75                  80
Glu Glu Asn Asn Leu Lys Asp Asp Leu Leu Tyr Lys Asn Ser Arg Leu
                 85                  90                  95
Glu Asn Glu Asp Phe Ile Val Thr Gly Glu Val Ile Phe Asn Thr Ala
                100                 105                 110
Met Val Gly Tyr Pro Glu Ala Leu Thr Asp Pro Ser Tyr Phe Gly Gln
            115                 120                 125
Ile Leu Val Leu Thr Phe Pro Ser Ile Gly Asn Tyr Gly Ile Glu Lys
            130                 135                 140
Val Lys His Asp Glu Thr Phe Gly Leu Val Gln Asn Phe Glu Ser Asn
145                 150                 155                 160
Lys Ile Gln Val Gln Gly Leu Val Ile Cys Glu Tyr Ser Lys Gln Ser
                165                 170                 175
Tyr His Tyr Asn Ser Tyr Ile Thr Leu Ser Glu Trp Leu Lys Ile Tyr
                180                 185                 190
Lys Ile Pro Cys Ile Gly Gly Ile Asp Thr Arg Ala Leu Thr Lys Leu
            195                 200                 205
Leu Arg Glu Lys Gly Ser Met Leu Gly Lys Ile Val Ile Tyr Lys Asn
    210                 215                 220
Arg Gln His Ile Asn Lys Leu Tyr Lys Glu Ile Asn Leu Phe Asp Pro
225                 230                 235                 240
Gly Asn Ile Asp Thr Leu Lys Tyr Val Cys Asn His Phe Ile Arg Val
                245                 250                 255
Ile Lys Leu Asn Asn Ile Thr Tyr Asn Tyr Lys Asn Lys Glu Glu Phe
                260                 265                 270
Asn Tyr Thr Asn Glu Met Ile Thr Asn Asp Ser Ser Met Glu Asp His
            275                 280                 285
Asp Asn Glu Ile Asn Gly Ser Ile Ser Asn Phe Asn Asn Cys Pro Ser
    290                 295                 300
Ile Ser Ser Phe Asp Lys Ser Glu Ser Lys Asn Val Ile Asn His Thr
305                 310                 315                 320
Leu Leu Arg Asp Lys Met Asn Leu Ile Thr Ser Ser Glu Glu Tyr Leu
                325                 330                 335
Lys Asp Leu His Asn Cys Asn Phe Ser Asn Ser Ser Lys Asn Asp
            340                 345                 350
Ser Phe Phe Lys Leu Tyr Gly Ile Cys Glu Tyr Asp Lys Tyr Leu Ile
            355                 360                 365
Asp Leu Glu Glu Asn Ala Ser Phe His Tyr Asn Asn Val Asp Glu Tyr
    370                 375                 380
Gly Tyr Tyr Asp Val Asn Lys Asn Thr Asn Ile Leu Ser Asn Asn Lys
385                 390                 395                 400
Ile Glu Gln Asn Asn Asn Asn Glu Asn Asn Lys Asn Asn Lys Asn Asn
                405                 410                 415
Asn Asn Asn Glu Val Asp Tyr Ile Lys Lys Asp Glu Asp Asn Asn Val
            420                 425                 430
Asn Ser Lys Val Phe Tyr Ser Gln Tyr Asn Asn Asn Ala Gln Asn Asn
            435                 440                 445
Glu His Thr Glu Phe Asn Leu Asn Asn Asp Tyr Ser Thr Tyr Ile Arg
    450                 455                 460
```

-continued

```
Lys Lys Met Lys Asn Glu Glu Phe Leu Asn Leu Val Asn Lys Arg Lys
465                 470                 475                 480

Val Asp His Lys Glu Lys Ile Ile Val Ile Val Asp Cys Gly Ile Lys
            485                 490                 495

Asn Ser Ile Ile Lys Asn Leu Ile Arg His Gly Met Asp Leu Pro Leu
        500                 505                 510

Thr Tyr Ile Ile Val Pro Tyr Tyr Asn Phe Asn His Ile Asp Tyr
    515                 520                 525

Asp Ala Val Leu Leu Ser Asn Gly Pro Gly Asp Pro Lys Lys Cys Asp
530                 535                 540

Phe Leu Ile Lys Asn Leu Lys Asp Ser Leu Thr Lys Asn Lys Ile Ile
545                 550                 555                 560

Phe Gly Ile Cys Leu Gly Asn Gln Leu Leu Gly Ile Ser Leu Gly Cys
                565                 570                 575

Asp Thr Tyr Lys Met Lys Tyr Gly Asn Arg Gly Val Asn Gln Pro Val
            580                 585                 590

Ile Gln Leu Val Asp Asn Ile Cys Tyr Ile Thr Ser Gln Asn His Gly
        595                 600                 605

Tyr Cys Leu Lys Lys Lys Ser Ile Leu Lys Arg Lys Glu Leu Ala Ile
    610                 615                 620

Ser Tyr Ile Asn Ala Asn Asp Lys Ser Ile Glu Gly Ile Ser His Lys
625                 630                 635                 640

Asn Gly Arg Phe Tyr Ser Val Gln Phe His Pro Glu Gly Asn Asn Gly
                645                 650                 655

Pro Glu Asp Thr Ser Phe Leu Phe Lys Asn Phe Leu Leu Asp Ile Phe
            660                 665                 670

Asn Lys Lys Lys Gln Tyr Arg Glu Tyr Leu Gly Tyr Asn Ile Ile Tyr
        675                 680                 685

Ile Lys Lys Lys Val Leu Leu Leu Gly Ser Gly Leu Cys Ile Gly
    690                 695                 700

Gln Ala Gly Glu Phe Asp Tyr Ser Gly Thr Gln Ala Ile Lys Ser Leu
705                 710                 715                 720

Lys Glu Cys Gly Ile Tyr Val Ile Leu Val Asn Pro Asn Ile Ala Thr
                725                 730                 735

Val Gln Thr Ser Lys Gly Leu Ala Asp Lys Val Tyr Phe Leu Pro Val
            740                 745                 750

Asn Cys Glu Phe Val Glu Lys Ile Ile Lys Lys Glu Lys Pro Asp Phe
        755                 760                 765

Ile Leu Cys Thr Phe Gly Gly Gln Thr Ala Leu Asn Cys Ala Leu Met
    770                 775                 780

Leu Asp Gln Lys Lys Val Leu Lys Lys Asn Asn Cys Gln Cys Leu Gly
785                 790                 795                 800

Thr Ser Leu Glu Ser Ile Arg Ile Thr Glu Asn Arg Thr Leu Phe Ala
                805                 810                 815

Glu Lys Leu Lys Glu Ile Asn Glu Arg Ile Ala Pro Tyr Gly Ser Ala
            820                 825                 830

Lys Asn Val Asn Gln Ala Ile Asp Ile Ala Asn Lys Ile Gly Tyr Pro
        835                 840                 845

Ile Leu Val Arg Thr Thr Phe Ser Leu Gly Gly Leu Asn Ser Ser Phe
    850                 855                 860

Ile Asn Asn Glu Glu Glu Leu Ile Glu Lys Cys Asn Lys Ile Phe Leu
865                 870                 875                 880

Gln Thr Asp Asn Glu Ile Phe Ile Asp Lys Ser Leu Gln Gly Trp Lys
```

```
                        885                 890                 895

Glu Ile Glu Tyr Glu Leu Leu Arg Asp Asn Lys Asn Asn Cys Ile Ala
                900                 905                 910

Ile Cys Asn Met Glu Asn Ile Asp Pro Leu Gly Ile His Thr Gly Asp
            915                 920                 925

Ser Ile Val Val Ala Pro Ser Gln Thr Leu Ser Asn Tyr Glu Tyr Tyr
        930                 935                 940

Lys Phe Arg Glu Ile Ala Leu Lys Val Ile Thr His Leu Asn Ile Ile
945                 950                 955                 960

Gly Glu Cys Asn Ile Gln Phe Gly Ile Asn Pro Gln Thr Gly Glu Tyr
                965                 970                 975

Cys Ile Ile Glu Val Asn Ala Arg Leu Ser Arg Ser Ser Ala Leu Ala
            980                 985                 990

Ser Lys Ala Thr Gly Tyr Pro Leu Ala Tyr Ile Ser Ala Lys Ile Ala
        995                 1000                1005

Leu Gly Tyr Asp Leu Ile Ser Leu Lys Asn Ser Ile Thr Lys Lys Thr
    1010                1015                1020

Thr Ala Cys Phe Glu Pro Ser Leu Asp Tyr Ile Thr Thr Lys Ile Pro
1025                1030                1035                1040

Arg Trp Asp Leu Asn Lys Phe Glu Phe Ala Ser Asn Thr Met Asn Ser
                1045                1050                1055

Ser Met Lys Ser Val Gly Glu Val Met Ser Ile Gly Arg Thr Phe Glu
            1060                1065                1070

Glu Ser Ile Gln Lys Ser Leu Arg Cys Ile Asp Asp Asn Tyr Leu Gly
        1075                1080                1085

Phe Ser Asn Thr Tyr Cys Ile Asp Trp Asp Glu Lys Lys Ile Ile Glu
    1090                1095                1100

Glu Leu Lys Asn Pro Ser Pro Lys Arg Ile Asp Ala Ile His Gln Ala
1105                1110                1115                1120

Phe His Leu Asn Met Pro Met Asp Lys Ile His Glu Leu Thr His Ile
                1125                1130                1135

Asp Tyr Trp Phe Leu His Lys Phe Tyr Asn Ile Tyr Asn Leu Gln Asn
            1140                1145                1150

Lys Leu Lys Thr Leu Lys Leu Glu Gln Leu Ser Phe Asn Asp Leu Lys
        1155                1160                1165

Tyr Phe Lys Lys His Gly Phe Ser Asp Lys Gln Ile Ala His Tyr Leu
    1170                1175                1180

Ser Phe Asn Thr Ser Asp Asn Asn Asn Asn Asn Asn Asn Ile Ser Ser
1185                1190                1195                1200

Cys Arg Val Thr Glu Asn Asp Val Met Lys Tyr Arg Glu Lys Leu Gly
                1205                1210                1215

Leu Phe Pro His Ile Lys Val Ile Asp Thr Leu Ser Ala Glu Phe Pro
            1220                1225                1230

Ala Leu Thr Asn Tyr Leu Tyr Leu Thr Tyr Gln Gly Gln Glu His Asp
        1235                1240                1245

Val Leu Pro Leu Asn Met Lys Arg Lys Lys Ile Cys Thr Leu Asn Asn
    1250                1255                1260

Lys Arg Asn Ala Asn Lys Lys Lys Val His Val Lys Asn His Leu Tyr
1265                1270                1275                1280

Asn Glu Val Val Asp Asp Lys Asp Thr Gln Leu His Lys Glu Asn Asn
                1285                1290                1295

Asn Asn Asn Asn Met Asn Ser Gly Asn Val Glu Asn Lys Cys Lys Leu
            1300                1305                1310
```

```
Asn Lys Glu Ser Tyr Gly Tyr Asn Asn Ser Ser Asn Cys Ile Asn Thr
    1315                1320                1325
Asn Asn Ile Asn Ile Glu Asn Asn Ile Cys His Asp Ile Ser Ile Asn
    1330                1335                1340
Lys Asn Ile Lys Val Thr Ile Asn Asn Ser Asn Asn Ser Ile Ser Asn
1345                1350                1355                1360
Asn Glu Asn Val Glu Thr Asn Leu Asn Cys Val Ser Glu Arg Ala Gly
            1365                1370                1375
Ser His His Ile Tyr Gly Lys Glu Glu Lys Ser Ile Gly Ser Asp Asp
            1380                1385                1390
Thr Asn Ile Leu Ser Ala Gln Asn Ser Asn Asn Phe Ser Cys Asn
    1395                1400                1405
Asn Glu Asn Met Asn Lys Ala Asn Val Asp Val Asn Val Leu Glu Asn
    1410                1415                1420
Asp Thr Lys Lys Arg Glu Asp Ile Asn Thr Thr Thr Val Phe Met Glu
1425                1430                1435                1440
Gly Gln Asn Ser Val Ile Asn Asn Lys Asn Lys Glu Asn Ser Ser Leu
            1445                1450                1455
Leu Lys Gly Asp Glu Glu Asp Ile Val Met Val Asn Leu Lys Lys Glu
            1460                1465                1470
Asn Asn Tyr Asn Ser Val Ile Asn Asn Val Asp Cys Arg Lys Lys Asp
            1475                1480                1485
Met Asp Gly Lys Asn Ile Asn Asp Glu Cys Lys Thr Tyr Lys Lys Asn
            1490                1495                1500
Lys Tyr Lys Asp Met Gly Leu Asn Asn Asn Ile Val Asp Glu Leu Ser
1505                1510                1515                1520
Asn Gly Thr Ser His Ser Thr Asn Asp His Leu Tyr Leu Asp Asn Phe
            1525                1530                1535
Asn Thr Ser Asp Glu Glu Ile Gly Asn Asn Lys Asn Met Asp Met Tyr
            1540                1545                1550
Leu Ser Lys Glu Lys Ser Ile Ser Asn Lys Asn Pro Gly Asn Ser Tyr
            1555                1560                1565
Tyr Val Val Asp Ser Val Tyr Asn Asn Glu Tyr Lys Ile Asn Lys Met
    1570                1575                1580
Lys Glu Leu Ile Asp Asn Glu Asn Leu Asn Asp Glu Tyr Asn Asn Asn
1585                1590                1595                1600
Val Asn Met Asn Cys Ser Asn Tyr Asn Asn Ala Ser Ala Phe Val Asn
            1605                1610                1615
Gly Lys Asp Arg Asn Asp Asn Leu Glu Asn Asp Cys Ile Glu Lys Asn
            1620                1625                1630
Met Asp His Thr Tyr Lys His Tyr Asn Arg Leu Asn Asn Arg Arg Ser
            1635                1640                1645
Thr Asn Glu Arg Met Met Leu Met Val Asn Asn Glu Lys Glu Ser Asn
    1650                1655                1660
His Glu Lys Gly His Arg Arg Asn Gly Leu Asn Lys Lys Asn Lys Glu
1665                1670                1675                1680
Lys Asn Met Glu Lys Asn Lys Gly Lys Asn Lys Asp Lys Lys Asn Tyr
            1685                1690                1695
His Tyr Val Asn His Lys Arg Asn Asn Glu Tyr Asn Ser Asn Asn Ile
            1700                1705                1710
Glu Ser Lys Phe Asn Asn Tyr Val Asp Asp Ile Asn Lys Lys Glu Tyr
    1715                1720                1725
```

-continued

Tyr Glu Asp Glu Asn Asp Ile Tyr Tyr Phe Thr His Ser Ser Gln Gly
    1730                1735                1740

Asn Asn Asp Asp Leu Ser Asn Asp Asn Tyr Leu Ser Ser Glu Glu Leu
1745                1750                1755                1760

Asn Thr Asp Glu Tyr Asp Asp Tyr Tyr Tyr Asp Glu Asp Glu Glu
        1765                1770                1775

Asp Asp Tyr Asp Asp Asp Asn Asp Asp Asp Asp Asp Asp Asp
    1780                1785                1790

Gly Glu Asp Glu Glu Asp Asn Asp Tyr Tyr Asn Asp Asp Gly Tyr Asp
    1795                1800                1805

Ser Tyr Asn Ser Leu Ser Ser Ser Arg Ile Ser Asp Val Ser Ser Val
    1810                1815                1820

Ile Tyr Ser Gly Asn Glu Asn Ile Phe Asn Glu Lys Tyr Asn Asp Ile
1825                1830                1835                1840

Gly Phe Lys Ile Ile Asp Asn Arg Asn Glu Lys Glu Lys Glu Lys Lys
        1845                1850                1855

Lys Cys Phe Ile Val Leu Gly Cys Gly Cys Tyr Arg Ile Gly Ser Ser
        1860                1865                1870

Val Glu Phe Asp Trp Ser Ala Ile His Cys Val Lys Thr Ile Arg Lys
    1875                1880                1885

Leu Asn His Lys Ala Ile Leu Ile Asn Cys Asn Pro Glu Thr Val Ser
    1890                1895                1900

Thr Asp Tyr Asp Glu Ser Asp Arg Leu Tyr Phe Asp Glu Ile Thr Thr
1905                1910                1915                1920

Glu Val Ile Lys Phe Ile Tyr Asn Phe Glu Asn Ser Asn Gly Val Ile
            1925                1930                1935

Ile Ala Phe Gly Gly Gln Thr Ser Asn Asn Leu Val Phe Ser Leu Tyr
        1940                1945                1950

Lys Asn Asn Val Asn Ile Leu Gly Ser Val His Lys Val Leu Ile Val
        1955                1960                1965

Val Lys Ile Gly Ile Asn Phe Arg Thr Tyr Val Ile Leu Lys Ile Asp
    1970                1975                1980

Gln Pro Lys Trp Asn Lys Phe Thr Lys Leu Ser Lys Ala Ile Gln Phe
1985                1990                1995                2000

Ala Asn Glu Val Lys Phe Pro Val Leu Val Arg Pro Ser Tyr Val Leu
            2005                2010                2015

Ser Gly Ala Ala Met Arg Val Val Asn Cys Phe Glu Glu Leu Lys Asn
        2020                2025                2030

Phe Leu Met Lys Ala Ala Ile Val Ser Lys Asp Asn Pro Val Val Ile
        2035                2040                2045

Ser Lys Phe Ile Glu Asn Ala Lys Glu Ile Glu Ile Asp Cys Val Ser
2050                2055                2060

Lys Asn Gly Lys Ile Ile Asn Tyr Ala Ile Ser Glu His Val Glu Asn
2065                2070                2075                2080

Ala Gly Val His Ser Gly Asp Ala Thr Leu Ile Leu Pro Ala Gln Asn
        2085                2090                2095

Ile Tyr Val Glu Thr His Arg Lys Ile Lys Lys Ile Ser Glu Lys Ile
            2100                2105                2110

Ser Lys Ser Leu Asn Ile Ser Gly Pro Phe Asn Ile Gln Phe Ile Cys
        2115                2120                2125

His Gln Asn Glu Ile Lys Ile Ile Glu Cys Asn Leu Arg Ala Ser Arg
    2130                2135                2140

Thr Phe Pro Phe Ile Ser Lys Ala Leu Asn Leu Asn Phe Ile Asp Leu

-continued

```
                2145                2150                2155                2160

Ala Thr Arg Ile Leu Met Gly Tyr Asp Val Lys Pro Ile Asn Ile Ser
            2165                2170                2175

Leu Ile Asp Leu Glu Tyr Thr Ala Val Lys Ala Pro Ile Phe Ser Phe
        2180                2185                2190

Asn Arg Leu His Gly Ser Asp Cys Ile Leu Gly Val Glu Met Lys Ser
    2195                2200                2205

Thr Gly Glu Val Ala Cys Phe Gly Leu Asn Lys Tyr Glu Ala Leu Leu
2210                2215                2220

Lys Ser Leu Ile Ala Thr Gly Met Lys Leu Pro Lys Lys Ser Ile Leu
2225                2230                2235                2240

Ile Ser Ile Lys Asn Leu Asn Asn Lys Leu Ala Phe Glu Glu Pro Phe
            2245                2250                2255

Gln Leu Leu Phe Leu Met Gly Phe Thr Ile Tyr Ala Thr Glu Gly Thr
        2260                2265                2270

Tyr Asp Phe Tyr Ser Lys Phe Leu Glu Ser Phe Asn Val Asn Lys Gly
    2275                2280                2285

Ser Lys Phe His Gln Arg Leu Ile Lys Val His Asn Lys Asn Ala Glu
2290                2295                2300

Asn Ile Ser Pro Asn Thr Thr Asp Leu Ile Met Asn His Lys Val Glu
2305                2310                2315                2320

Met Val Ile Asn Ile Thr Asp Thr Leu Lys Thr Lys Val Ser Ser Asn
            2325                2330                2335

Gly Tyr Lys Ile Arg Arg Leu Ala Ser Asp Phe Gln Val Pro Leu Ile
        2340                2345                2350

Thr Asn Met Lys Leu Cys Ser Leu Phe Ile Asp Ser Leu Tyr Arg Lys
    2355                2360                2365

Phe Ser Arg Gln Lys Glu Arg Lys Ser Phe Tyr Thr Ile Lys Ser Tyr
2370                2375                2380

Asp Glu Tyr Ile Ser Leu Val
2385            2390

<210> SEQ ID NO 3
<211> LENGTH: 21
<212> TYPE: DNA
<213> ORGANISM: Plasmodium falciparum

<400> SEQUENCE: 3
ttttctaatc gactattttt a                                              21

<210> SEQ ID NO 4
<211> LENGTH: 21
<212> TYPE: DNA
<213> ORGANISM: Plasmodium falciparum

<400> SEQUENCE: 4
gacatacttg gacaattatt a                                              21

<210> SEQ ID NO 5
<211> LENGTH: 21
<212> TYPE: DNA
<213> ORGANISM: Plasmodium falciparum

<400> SEQUENCE: 5
ccttactatt gacattatta t                                              21

<210> SEQ ID NO 6
```

-continued

```
<210> SEQ ID NO 7
<211> LENGTH: 21
<212> TYPE: DNA
<213> ORGANISM: Plasmodium falciparum

<400> SEQUENCE: 6
ggctataaaa gaccttacta t                                              21

<210> SEQ ID NO 7
<211> LENGTH: 21
<212> TYPE: DNA
<213> ORGANISM: Plasmodium falciparum

<400> SEQUENCE: 7
ggatctccag gaccattaga t                                              21

<210> SEQ ID NO 8
<211> LENGTH: 21
<212> TYPE: DNA
<213> ORGANISM: Plasmodium falciparum

<400> SEQUENCE: 8
cctaaacatt gacaattatt c                                              21

<210> SEQ ID NO 9
<211> LENGTH: 21
<212> TYPE: DNA
<213> ORGANISM: Plasmodium falciparum

<400> SEQUENCE: 9
tcatgttctt gaccttgata a                                              21

<210> SEQ ID NO 10
<211> LENGTH: 21
<212> TYPE: DNA
<213> ORGANISM: Plasmodium falciparum

<400> SEQUENCE: 10
gatatatcat gacaaatatt a                                              21

<210> SEQ ID NO 11
<211> LENGTH: 21
<212> TYPE: DNA
<213> ORGANISM: Plasmodium falciparum

<400> SEQUENCE: 11
gttaccttgt gacgaatgtg t                                              21

<210> SEQ ID NO 12
<211> LENGTH: 21
<212> TYPE: DNA
<213> ORGANISM: Plasmodium falciparum

<400> SEQUENCE: 12
tcattttgat gacatataaa t                                              21

<210> SEQ ID NO 13
<211> LENGTH: 29
<212> TYPE: DNA
<213> ORGANISM: Plasmodium falciparum

<400> SEQUENCE: 13
aacatcatgt tcttgacctt gataagtta                                      29
```

```
<210> SEQ ID NO 14
<211> LENGTH: 21
<212> TYPE: DNA
<213> ORGANISM: Plasmodium falciparum

<400> SEQUENCE: 14
cgtcggaact gaatttggct c                                          21

<210> SEQ ID NO 15
<211> LENGTH: 21
<212> TYPE: DNA
<213> ORGANISM: Plasmodium falciparum

<400> SEQUENCE: 15
cctcagtgct gacagcccat c                                          21
```